United States Patent
Zhao et al.

(10) Patent No.: US 11,261,483 B2
(45) Date of Patent: Mar. 1, 2022

(54) PROGRAMMABLE DNA-GUIDED ARTIFICIAL RESTRICTION ENZYMES

(71) Applicant: The Board of Trustees of the University of Illinois, Urbana, IL (US)

(72) Inventors: Huimin Zhao, Champaign, IL (US); Behnam Enghiad, Urbana, IL (US)

(73) Assignee: BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 15/806,621

(22) Filed: Nov. 8, 2017

(65) Prior Publication Data

US 2021/0087604 A1   Mar. 25, 2021

Related U.S. Application Data

(60) Provisional application No. 62/419,692, filed on Nov. 9, 2016.

(51) Int. Cl.
| | |
|---|---|
| *C12Q 1/683* | (2018.01) |
| *C12N 15/66* | (2006.01) |
| *C12N 1/20* | (2006.01) |
| *C12N 9/22* | (2006.01) |
| *C12Q 1/686* | (2018.01) |

(52) U.S. Cl.
CPC .......... *C12Q 1/683* (2013.01); *C12N 1/20* (2013.01); *C12N 9/22* (2013.01); *C12N 15/66* (2013.01); *C12Q 1/686* (2013.01)

(58) Field of Classification Search
None
See application file for complete search history.

(56) References Cited

U.S. PATENT DOCUMENTS

9,902,973 B2 * 2/2018 Van Der Oost ........ C12N 15/10
2006/0141600 A1   6/2006 Joshua-tor

FOREIGN PATENT DOCUMENTS

| WO | 2007048629 A2 | 3/2007 |
| WO | 2014189628 A1 | 11/2014 |
| WO | 2015157534 A1 | 10/2015 |
| WO | 2016028843 A2 | 2/2016 |

OTHER PUBLICATIONS

Swarts et al., Nature Structural & Molecular Biology, vol. 21, No. 9, pp. 743-753, 2014.*
Enghiad et al., "Programmable DNA-Guided Artificial Restriction Enzymes", ACS Synth Biol., 6:752-757 (2017).
Gao et al., "DNA-guided genome editing using the Natronobacterium gregoryi Argonaute", Nature Biotechnology, 34(7):768-773 (2016).
Hock et al., "The Argonaute protein family", Genome Biology, 9:210 (2008).
Jiang et al., "Cas9-Assisted Targeting of CHromosome segments CATCH enables one-step targeted cloning of large gene clusters", Nature Communications, p. 1-8 (2015).

(Continued)

*Primary Examiner* — Richard G Hutson
(74) *Attorney, Agent, or Firm* — DLA Piper LLP (US)

(57) ABSTRACT

Methods and compositions for specific cleavage of DNA molecules using single-stranded guides and Argonaute (Ago) proteins are described.

10 Claims, 14 Drawing Sheets

Specification includes a Sequence Listing.

Overview of the *Pf*Ago/ARE platform.

(56) References Cited

OTHER PUBLICATIONS

Jinek et al., "A Programmable Dual-RNA-Guided DNA Endonuclease in Adaptive Bacterial Immunity", Science, 337:816-821 (2012).
Kaya et al., "A bacterial Argonaute with noncanonical guide RNA specificity", PNAS, 113(15):4057-4062 (2016).
Makarova et al., "Prokaryotic homologs of Argonaute proteins are predicted to function as key components of a novel system of defense against mobile genetic elements", Biology Direct, 4:29 (2009).
Meister "Argonaute proteins: functional insights and emerging roles", NatureReviews Genetics, 14(7):447-459 (2013).
Swarts et al., "DNA-guided DNA interference by a prokaryotic Argonaute", Nature, 507(7491):258-261 (2014).
Swarts et al., "Argonaute of the archaeon Pyrococcus furiosus is a DNA-guided nuclease that targets cognate DNA", Nucleic Acids Research, 43(10):5120-5129 (2015).

\* cited by examiner

Fig. 1. Overview of the *Pf*Ago/ARE platform.

Fig. 2. PCR cloning experiments.

Fig. 3. DNA fingerprinting experiments.

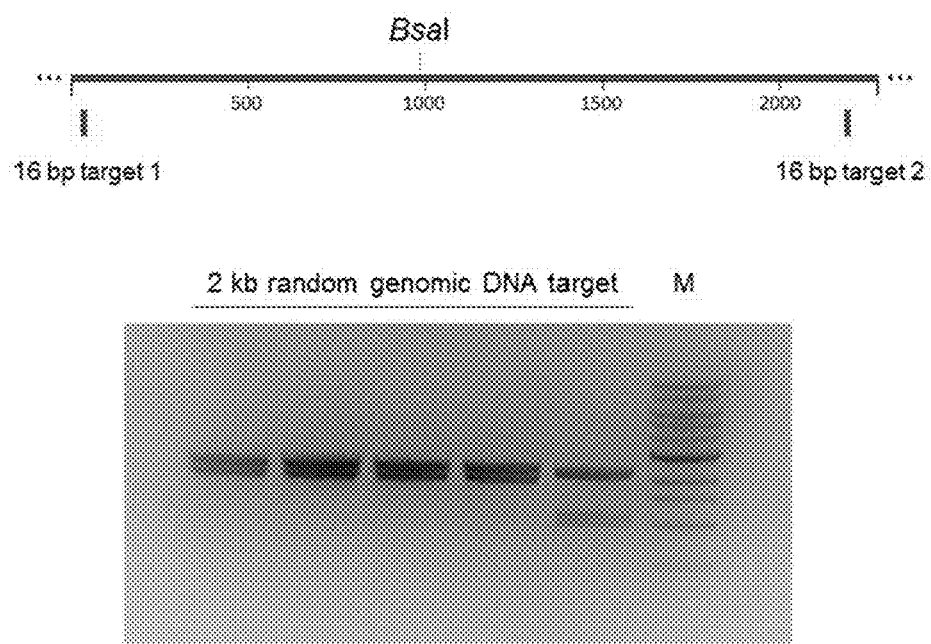
Fig. 8. Genomic DNA cloning using *Pf*Ago/AREs.

Fig. 9

A. Codon-optimized *PfAgo* gene for high-level expression in *E. coli* (SEQ ID NO:67)

```
atgaaggcgaaggttgtgatcaacctggttaagatcaacaagaaaatcatcccggataagatttacgtttaccgtctg
ttcaacgacccggaggaagagctgcagaaagagggttatagcatctaccgtctggcgtatgaaaacgtgggcatcgtt
attgatccggagaacctgatcattgcgaccaccaaggagctggaatacgagggcgagttcatcccggagggcgaaatt
agctttagcgaactgcgtaacgactatcaaagcaagctggtgctgcgtctgctgaaagagaacggtatcggcgagtac
gaactgagcaaactgctgcgtaagttccgtaagccgaaaacctttggtgactataaagtgatcccgagcgttgaaatg
agcgtgattaagcacgacgaggatttctacctggttatccacatcattcaccagattcaaagcatgaaaaccctgtgg
gaactggtgaacaaggacccgaaagagctggaagagttcctgatgacccacaaggaaaacctgatgctgaaagacatc
gcgagcccgctgaaaaccgtttataagccgtgctttgaagagtacaccaagaaaccgaaactggatcacaaccaggaa
attgtgaagtactggtataactaccacatcgagcgttattggaacaccccggaagcgaagctggagttctaccgtaaa
tttggccaggttgacctgaagcaaccggcgatcctggcgaaatttgcgagcaagattaagaaaaacaagaactacaaa
atctacctgctgccgcagctggttgtgccgacctataacgcggaacaactggagagcgatgttgcgaaggaaattctg
gagtacaccaaactgatgccggaagagcgtaaggaactgctggagaacatcctggcggaagtggacagcgacgatcatt
gacaaaagcctgagcgagatcgaagttgagaagattgcgcaggaactggagaacaaaattcgtgtgcgtgacgataag
ggtaacagcgttccgatcagccaactgaacgtgcagaaaagccaactgctgctgtggaccaactatagccgtaagtac
ccggttatcctgccgtacgaagtgccggagaagttccgtaaaatccgtgaaattccgatgtttatcattctggacagc
ggcctgctggcggacatccagaacttcgcgaccaacgaatttcgtgagctggtgaaaagcatgtactatagcctggcg
aagaaatacaacagcctggcgaagaaagcgcgtagcaccaacgagattggtctgccgttcctggattttcgtggcaag
gaaaaagttatcaccgaggacctgaacagcgataagggtatcattgaagtggttgagcaagtgagcagcttcatgaag
ggtaagaactgggcctggcgtttatcgcggcgcgtaacaaactgagcagcgagaagttcgaagagattaaacgtcgt
ctgtttaacctgaacgttatcagccaggtggttaacgaagataccctgaagaacaaacgtgacaaatatgatcgtaac
cgtctggacctgttcgttcgtcacaacctgctgtttcaagtgctgagcaaactgggtgttaagtactatgtgctggac
taccgtttcaactacgattacatcatcggtatcgacgtggcgccgatgaagcgtagcgaaggctatatcggtggcagc
gcggttatgtttgacagccagggctacatccgtaagattgtgccgatcaaaattggtgaacaacgtggcgagagcgtt
gatatgaacgagttcttcaaagagatggtggacaagttcaaagagtttaacatcaagctggataacaagaaaattctg
ctgctgcgtgacggtcgtattaccaacaacgaagaggaaggcctgaaatacatcagcgaaatgttcgatattgaggtg
gttacgatggacgttatcaaaaaccacccggtgcgtgcgttcgcgaacatgaagatgtattttaacctgggtggcgcg
atctacctgattccgcacaagctgaaacaggcgaaaggcaccccgatcccgattaagctggcgaagaaacgtatcatt
aagaacggcaaagttgagaagcagagcattacccgtcaagacgtgctggacatcttcattctgacccgtctgaactat
ggtagcatcagcgcggacatgcgtctgccggcgccggttcactatgcgcacaagtttgcgaacgcgatccgtaatgaa
tggaagatcaaagaggagtttctggcggagggttttctgtatttcgtgtaa
```

B. PfAgo amino acid sequence (SEQ ID NO:66)

```
MKAKVVINLVKINKKIIPDKIYVYRLFNDPEEELQKEGYSIYRLAYENVGIVIDPENLIIATTKELEYEGEFIPEGEI
SFSELRNDYQSKLVLRLLKENGIGEYELSKLLRKFRKPKTFGDYKVIPSVEMSVIKHDEDFYLVIHIIHQIQSMKTLW
ELVNKDPKELEEFLMTHKENLMLKDIASPLKTVYKPCFEEYTKKPKLDHNQEIVKYWYNYHIERYWNTPEAKLEFYRK
FGQVDLKQPAILAKFASKIKKNKNYKIYLLPQLVVPTYNAEQLESDVAKEILEYTKLMPEERKELLENILAEVDSDII
DKSLSEIEVEKIAQELENKIRVRDDKGNSVPISQLNVQKSQLLLWTNYSRKYPVILPYEVPEKFRKIREIPMFIILDS
GLLADIQNFATNEFRELVKSMYYSLAKKYNSLAKKARSTNEIGLPFLDFRGKEKVITEDLNSDKGIIEVVEQVSSFMK
GKELGLAFIAARNKLSSEKFEEIKRRLFNLNVISQVVNEDTLKNKRDKYDRNRLDLFVRHNLLFQVLSKLGVKYYVLD
YRFNYDYIIGIDVAPMKRSEGYIGGSAVMFDSQGYIRKIVPIKIGEQRGESVDMNEFFKEMVDKFKEFNIKLDNKKIL
LLRDGRITNNEEEGLKYISEMFDIEVVTMDVIKNHPVRAFANMKMYFNLGGAIYLIPHKLQAKGTPIPIKLAKKRII
KNGKVEKQSITRQDVLDIFILTRLNYGSISADMRLPAPVHYAHKFANAIRNEWKIKEEFLAEGFLYFV*
```

PROGRAMMABLE DNA-GUIDED ARTIFICIAL RESTRICTION ENZYMES

PRIORITY

This application claims the benefit of U.S. Ser. No. 62/419,692 filed on Nov. 9, 2016, which is incorporated herein by reference in its entirety.

BACKGROUND

Restriction enzymes are bacterial proteins that recognize specific DNA sequences and cut DNA at or near the recognition site. They were discovered in bacteria in the late 1960s (1-3) and have become the cornerstone of recombinant DNA technology since the early 1970s (4). So far more than 3600 restriction enzymes with >250 distinct specificities have been characterized (5), in which >250 are now commercially available for routine use in molecular biology. Most of them (i.e. type II restriction enzymes) only recognize short DNA sequences (4-8 base pairs), which significantly limits their application in recombinant DNA technology. Protein engineering was used to alter the sequence specificity of naturally occurring restriction enzymes, but met with limited success (6). Alternatively, artificial restriction enzymes (AREs) have been generated by fusing a DNA binding domain to a nuclease domain (e.g. zinc finger nucleases (ZFNs) (7) and transcription activator-like effector nucleases (TALENs) (8)) or using the clustered regularly interspaced short palindromic repeat (CRISPR)-associated enzyme 9 (Cas9) in vitro (9). Such AREs had higher specificity than naturally occurring restriction enzymes. However, they did not generate defined sticky or blunt ends, a hallmark of restriction enzymes, and showed rather poor activity due to their single or extremely low turnover numbers. Moreover, it is difficult to obtain them in sufficient amount and purity. All these limitations significantly constrain their applications in vitro.

SUMMARY

Restriction enzymes are essential tools for recombinant DNA technology that have revolutionized modern biological research. However, they have limited sequence specificity and availability. Provided herein are Argonaute (Ago) protein-based platforms for generating artificial restriction enzymes (AREs) capable of recognizing and cleaving DNA sequences at virtually any arbitrary site and generating defined sticky ends of varying length or blunt ends. Short DNA guides are used to direct Ago to target sites for cleavage at high temperatures followed by re-annealing of the cleaved single-stranded DNAs. These platforms have been used to generate over 18 AREs for DNA fingerprinting, molecular cloning of PCR-amplified or genomic DNAs, DNA assembly, and other uses. These AREs work as efficiently as their naturally occurring counterparts and some of them even do not have any naturally occurring counterparts, demonstrating easy programmability, generality, versatility, and high efficiency for this AREs technology.

Highly active artificial restriction enzymes with virtually any sequence specificity and defined sticky ends of varying length can be designed using the compositions and methods described herein.

TCGCCAAGCTTGCATG;                                      (SEQ ID NO: 33)

TATGCAAGCTTGGCGT;                                      (SEQ ID NO: 34)

NNNNNNNNNNNNNNCATGCAAGCTTGGCGTNNNNNNNNNNNNNN;         (SEQ ID NO: 115)

NNNNNNNNNNNNNNACGCCAAGCTTGCATGNNNNNNNNNNNNNN;         (SEQ ID NO: 116)

NNNNNNNNNNNNNNCATGCA;                                  (SEQ ID NO: 117)

AGCTTGGCGTNNNNNNNNNNNNNN;                              (SEQ ID NO: 118)

AGCTTGCATGNNNNNNNNNNNNNN;                              (SEQ ID NO: 119)

NNNNNNNNNNNNNNACGCCA.                                  (SEQ ID NO: 120)

Figure 2:
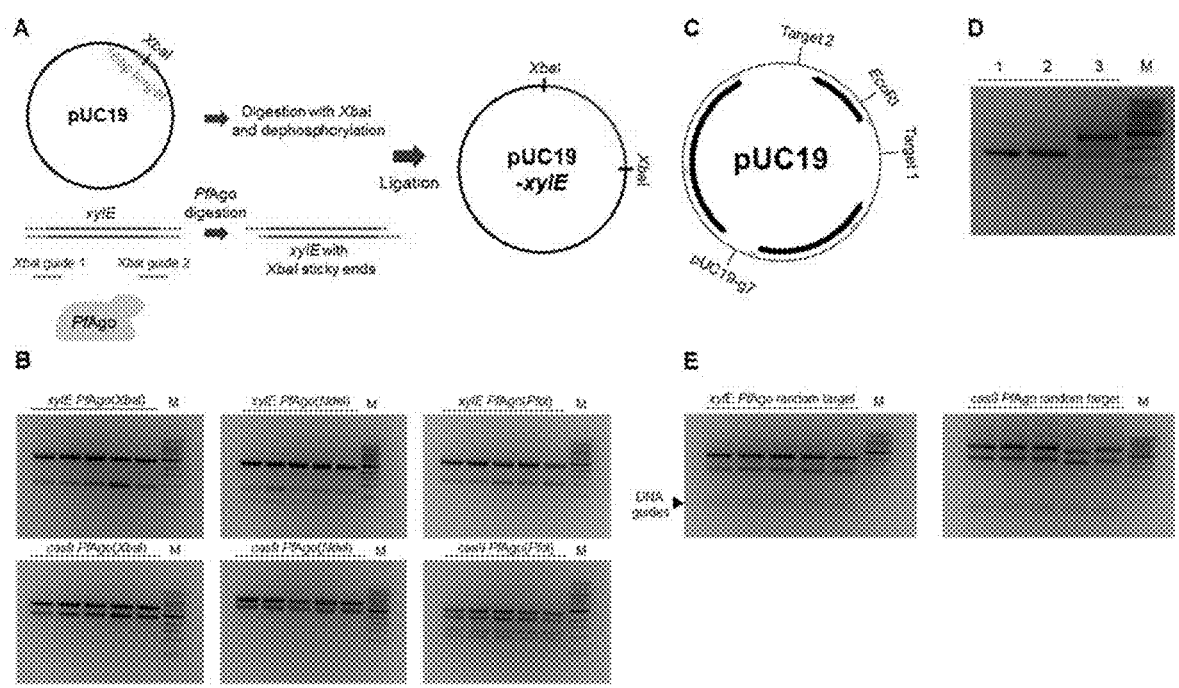

FIG. 2. PCR cloning experiments. A. An example of proof of concept PCR cloning using PfAgo/AREs. B. Restriction digestion check for correct cloning of PCR products digested with PfAgo(XbaI), PfAgo(NdeI), PfAgo(PfoI) AREs. Assembled plasmids were digested by corresponding native restriction enzymes. C. General map of pUC19 plasmid with positions of pUC19-g7, random target cloning sites and EcoRI digestion site indicated. D. Digestion analysis of negatively supercoiled pUC19 plasmid with PfAgo using EcoRI guides alone (lane 2) or EcoRI guides with addition of pUC19-g7 (lane 3). A negatively supercoiled pUC19 plasmid was run as control (lane 1). E. PfAgo-based digestion analysis for correct cloning of PCR products at a random target. DNA guides used for PfAgo cleavage are shown with a black triangle.

Figure 3:
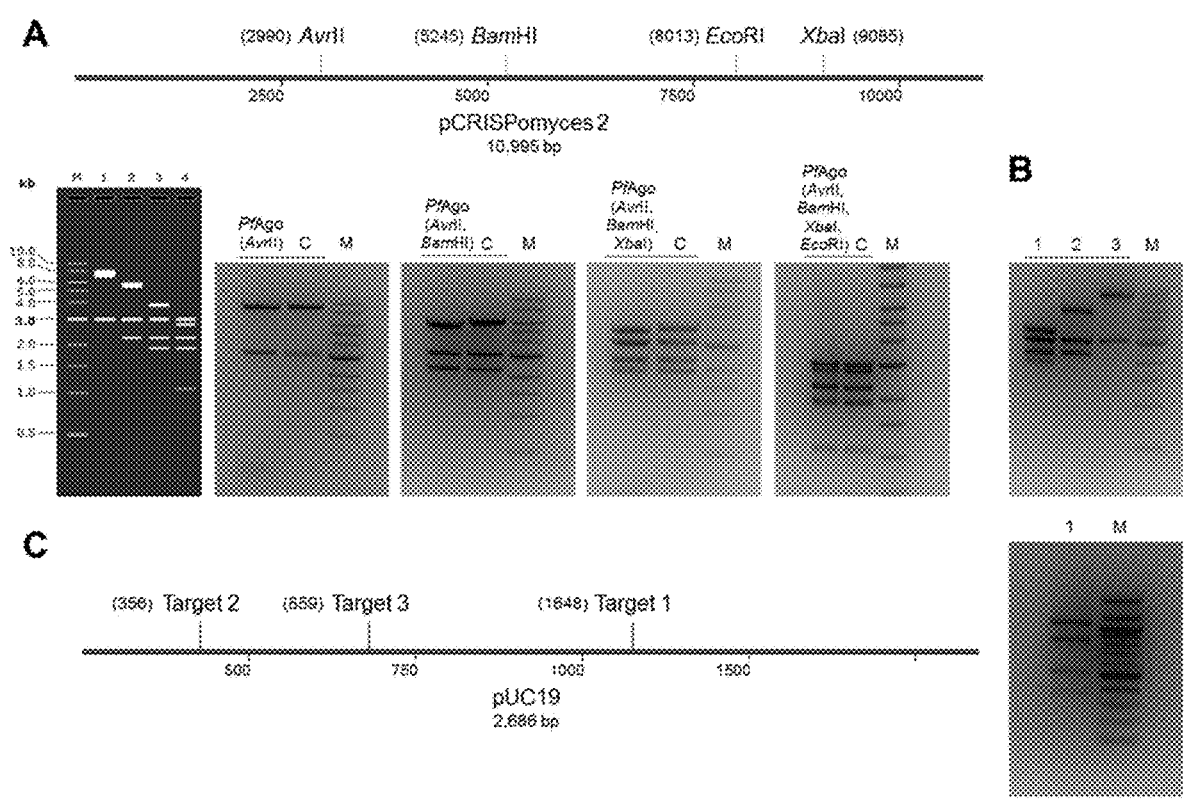

FIG. 3. DNA fingerprinting experiments. A. pCM2 DNA fingerprinting experiments. Linearized pCM2 (with Bsu36I) was digested with combinations of PfAgo/AREs. The same reactions were run using respective restriction enzymes instead of PfAgo to serve as positive control (shown by C). An overall map of linear pCM2 is also shown. B. Lane 1: Linearized pCM2 was digested using PfAgo with AvrII, BamHI, XbaI guides. Lane 2: one of the XbaI guides was excluded from the reaction. Lane 3: one of the XbaI and one of the BamHI guides were excluded from the reaction. C. pUC19 fingerprinting experiment. Linearized pUC19 (with BsaI) was digested with PfAgo at three different random targets to create the correct pattern (lane 1).

Figure 4:
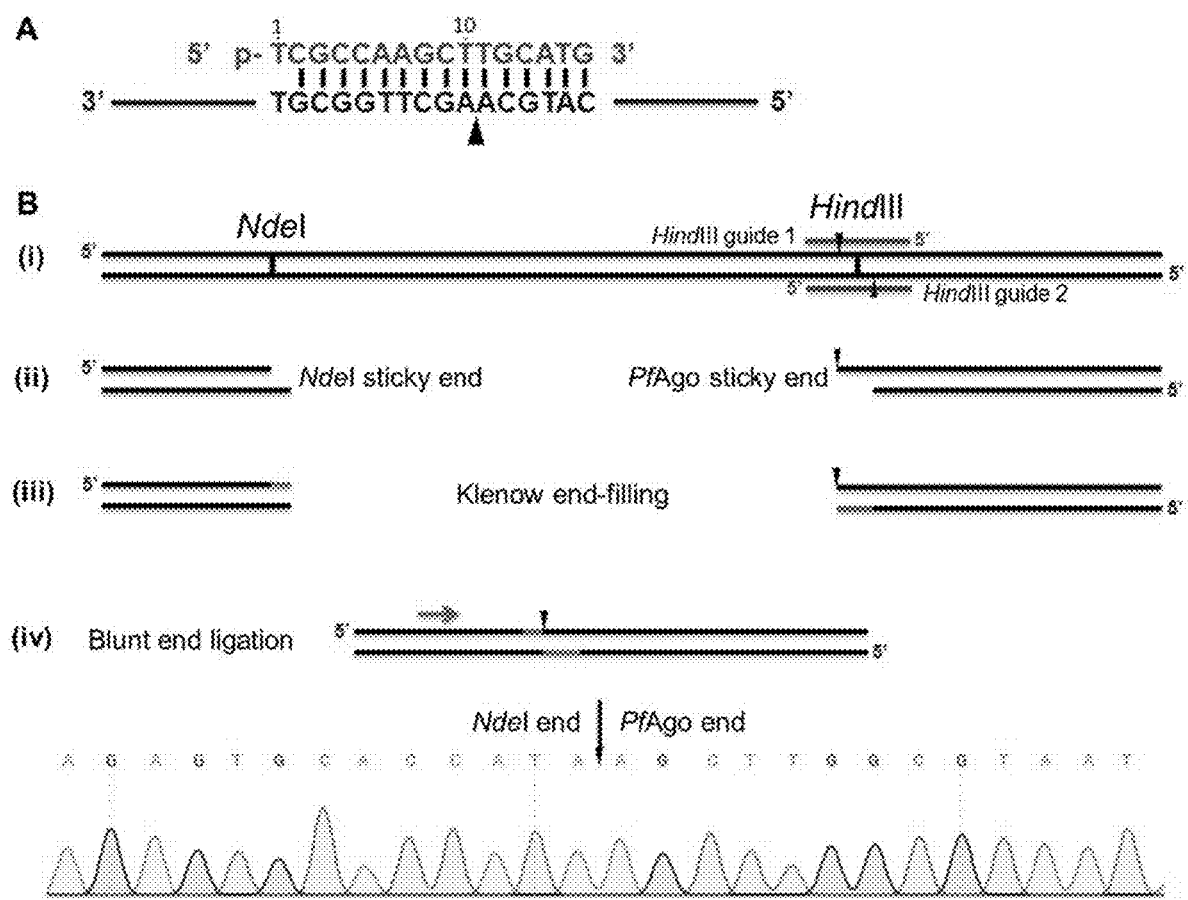

FIG. 4. PfAgo cleaves its ssDNA target between 10 and 11 nt position of its ssDNA guide. A. Expected cleavage site of PfAgo. The cleavage site is indicated by a black triangle. The guide and target sequences are shown with red and blue colors respectively. TCGCCAAGCTTGCATG is SEQ ID NO:33; CATGCAAGCTTGGCGT is SEQ ID NO:121. B. PfAgo cleavage site analysis. (i) pUC19 plasmid was linearized by NdeI and PfAgo using DNA guides which are expected to generate HindIII sticky ends. (ii) NdeI generates 5' sticky ends with 2 nt and PfAgo is expected to create 5' sticky ends of 4 nt. (iii) The 5' sticky ends were filled by Klenow fragment polymerase to create blunt ends. (iv) The two blunt ends were ligated together using T4 DNA ligase and the assembled plasmids were sent for DNA sequencing (AGAGTGCACCATAAGCTTGGCGTAAT is SEQ ID NO:122). The sequencing results confirmed expected cleavage site.

Figure 5:
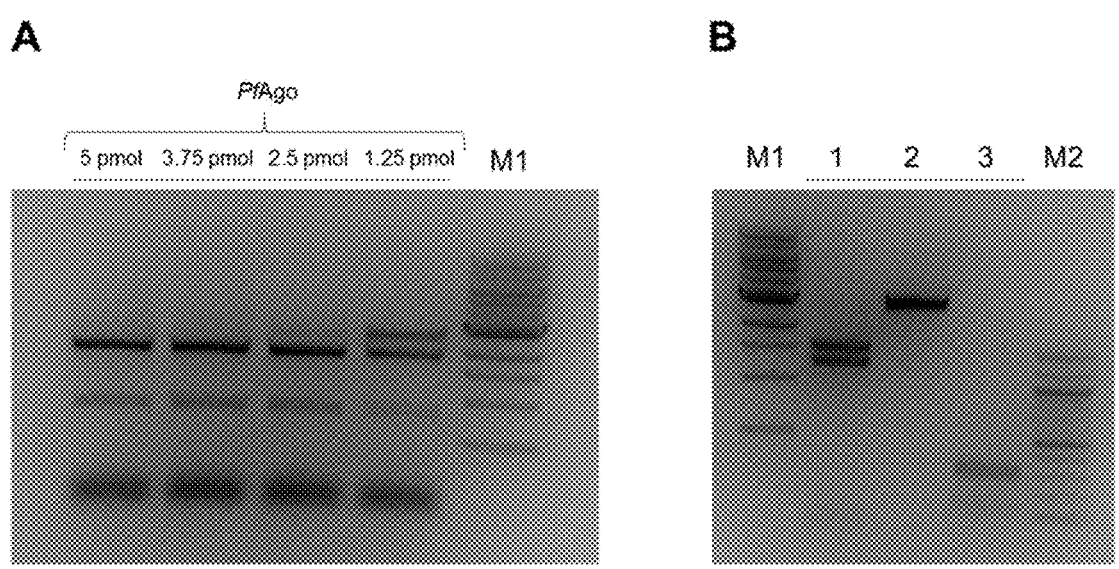

FIG. 5. Panel A. PfAgo activity assay. 1 µg of linear pUC19 plasmid (linearized with XmnI) was digested with PfAgo in a total of 50 µl reaction buffer supplemented with 5% (v/v) DMSO and 2.5 µM of each EcoRI guide. The reaction was incubated at 95° C. for 10 min with different PfAgo amounts. Panel B. PfAgo was able to cleave methylated dsDNA target. Lane 1: linear pUC19 (linearized with BsaI) was digested with PfAgo and MboI guides. Lane 2: linear pUC19 was incubated with MboI restriction enzyme. MboI was not able to digest the target due to methylation. Lane 3: a ~400 bp PCR product corresponding to the same MboI restriction site was digested with MboI as positive control. M1: 1 kb DNA ladder. M2: 100 bp DNA ladder.

Figure 6:
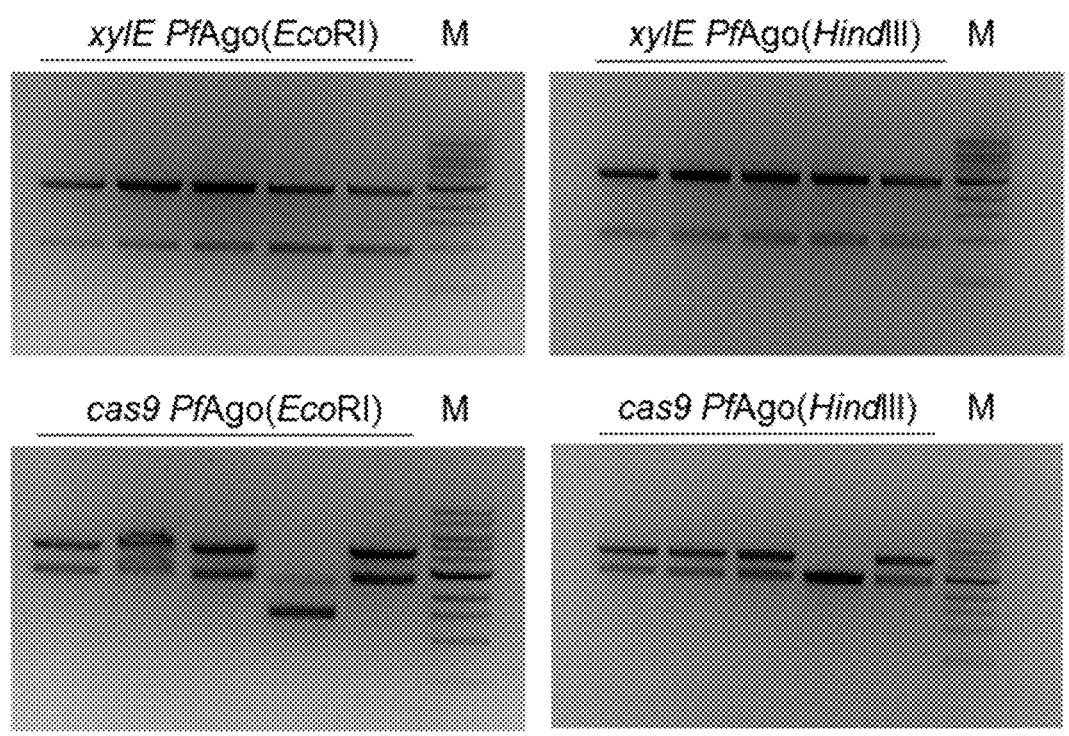

FIG. 6. Restriction digestion analysis of correct cloning of PCR products digested with PfAgo(EcoRI) and PfAgo(HindIII). The pUC19 vector was digested with corresponding native restriction enzymes.

Figure 7:
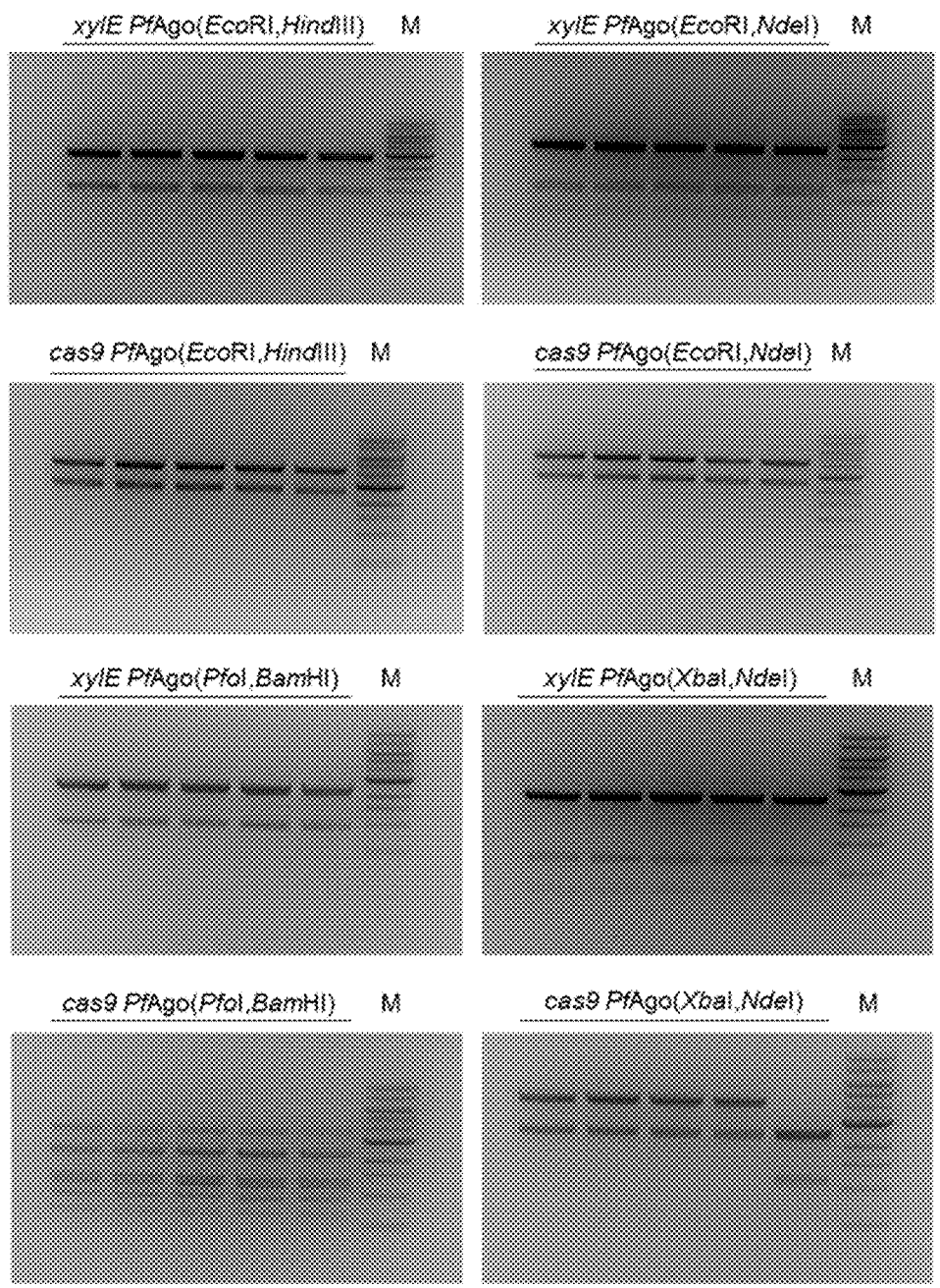

FIG. 7. Restriction digestion analysis of correct cloning of PCR products digested with PfAgo(EcoRI,HindIII), PfAgo (EcoRI,NdeI), PfAgo(PfoI,BamHI), and PfAgo(XbaI,NdeI). The pUC19 vector was also digested with the same PfAgo/AREs.

FIG. 8. Genomic DNA cloning using PfAgo/AREs. A random ~2 kb target from *S. coelicolor* A3(2) genomic DNA was cloned into pUC19 receiver backbone. *S. coelicolor* genomic DNA was digested with PfAgo/AREs targeting two ends of the 2 kb target (shown as bars above "16 bp target 1" and "16 bp target 2"). Restriction digestion of the assembled plasmids with BsaI showed 80% correct cloning. DNA sequencing results also confirmed the correct assembly.

FIG. 9. Panel A. Codon-optimized PfAgo gene for high-level expression in *E. coli* (SEQ ID NO:67). Panel B. PfAgo amino acid sequence (SEQ ID NO:66).

Figure 10:
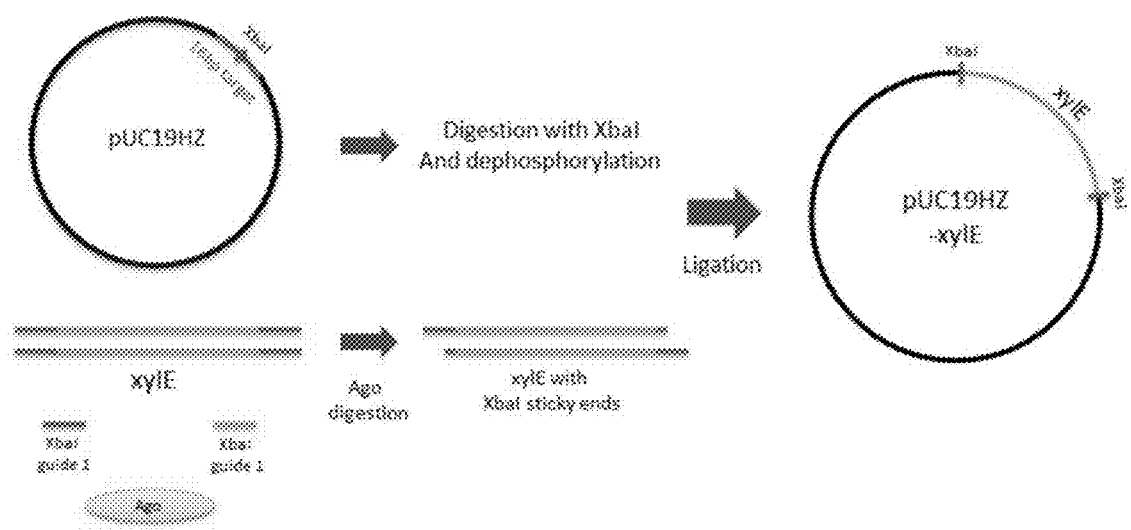

FIG. 10 shows an example of PCR cloning using ttAgo. The PCR insert was cleaved by ttAgo using XbaI guides at two sites to generate XbaI sticky ends on each end. The digested product was ligated into a backbone digested with XbaI restriction enzyme.

Figure 11:
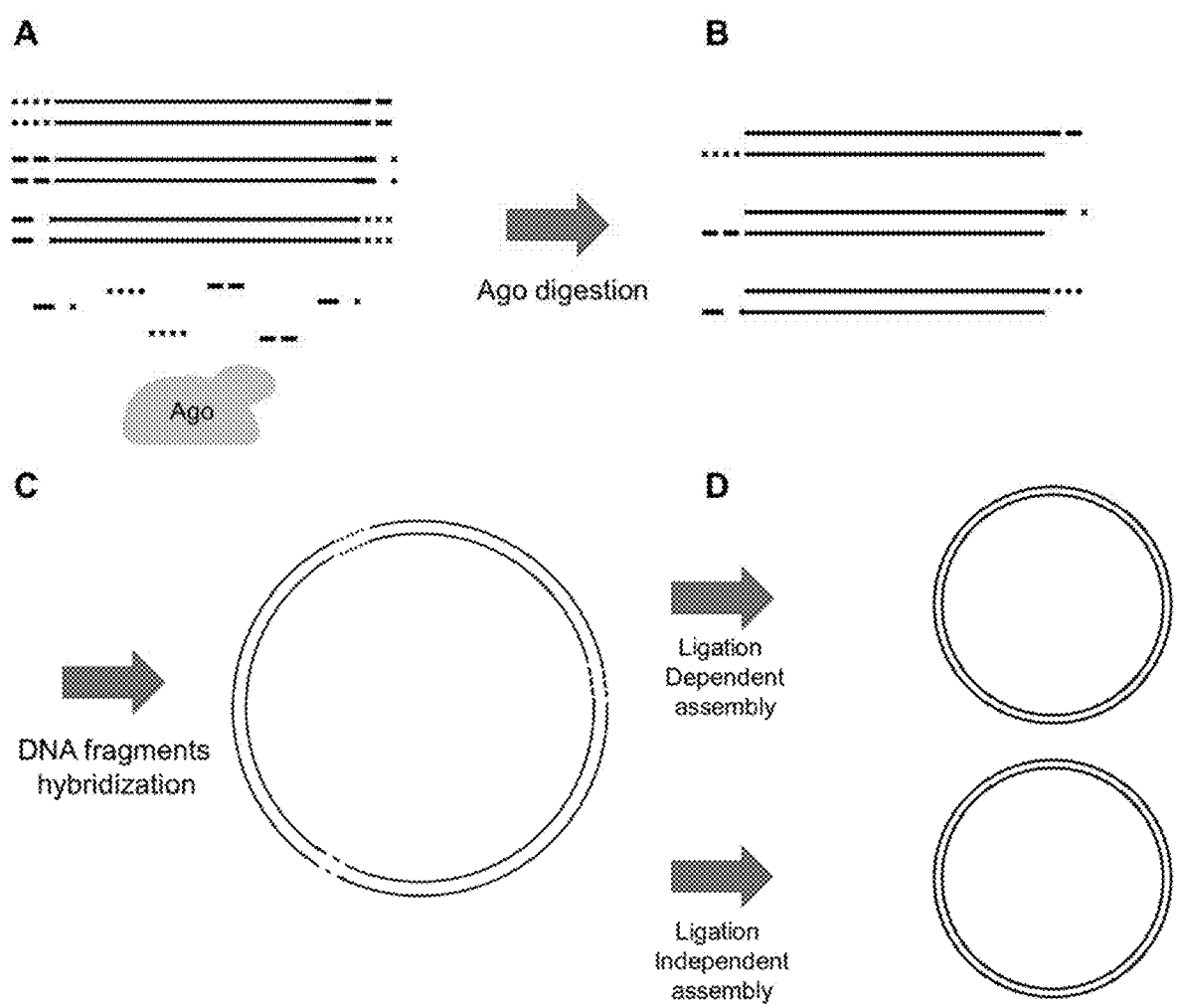

FIG. 11 shows a schematic representation for assembly of 3 DNA fragments using Ago-based AREs. A. Argonaute proteins are mixed with DNA guides to form Ago-based AREs. The formed AREs are mixed with DNA fragments in a one-pot or separate reactions. B. After Ago digestion, each fragment is left with the desired sticky ends on each ends. C. DNA fragments are able to hybridize with each other based on appropriate sticky end hybridization. D. The hybridized DNA fragments could be assembled together using ligation dependent or ligation independent methods.

Figure 12:
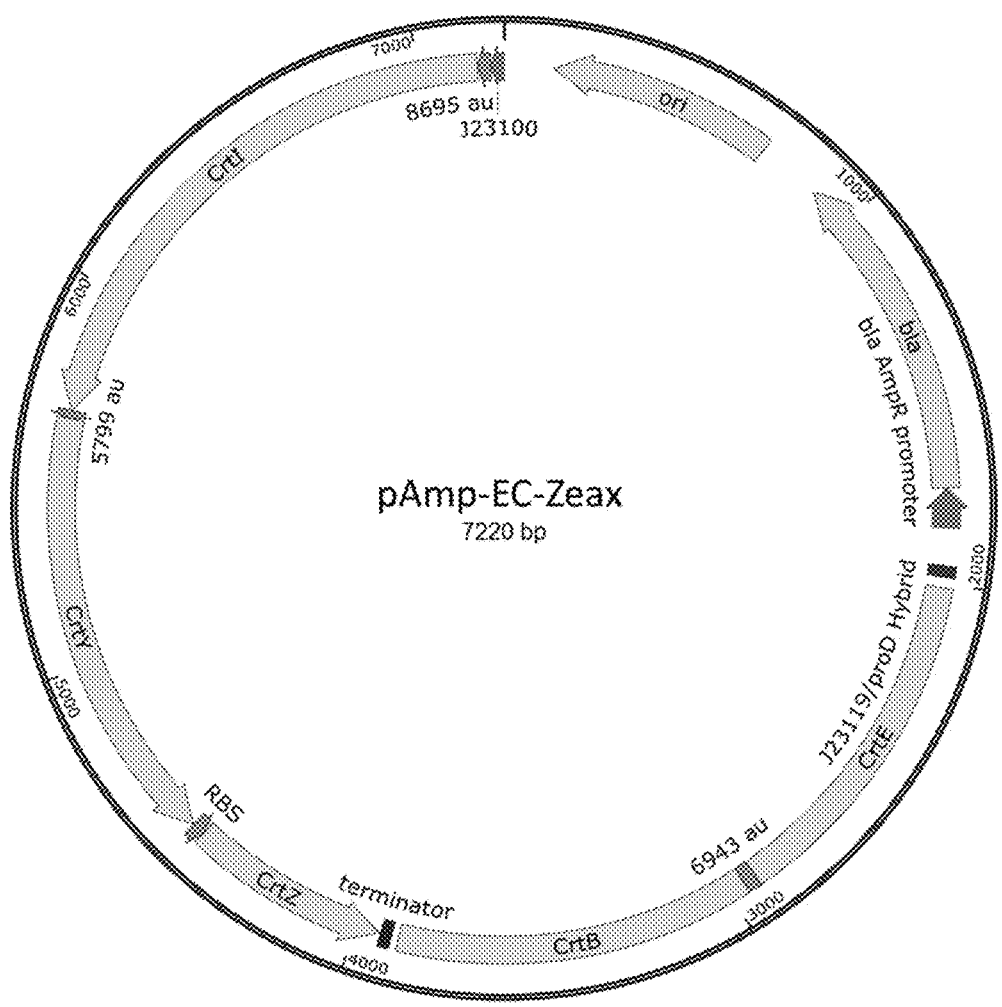

FIG. 12 shows a plasmid map for pAmp-EC-Zeax harboring the zeaxanthin pathway.

Figure 13:
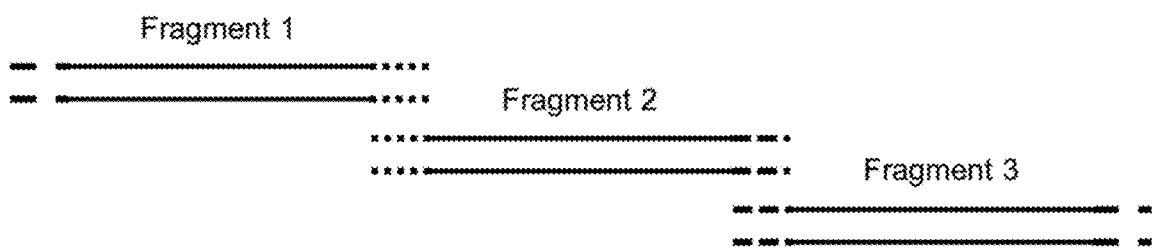

FIG. 13 shows the design of primers for DNA assembly in Example 7. Fragments were PCR amplified using primers so that each fragment shares 10 bp overlap with the previous and next fragment. After PfAgo digestion, the 10 nt sticky ends generated at each end can hybridize with the complementary sticky end generated on other fragments.

Figure 14:
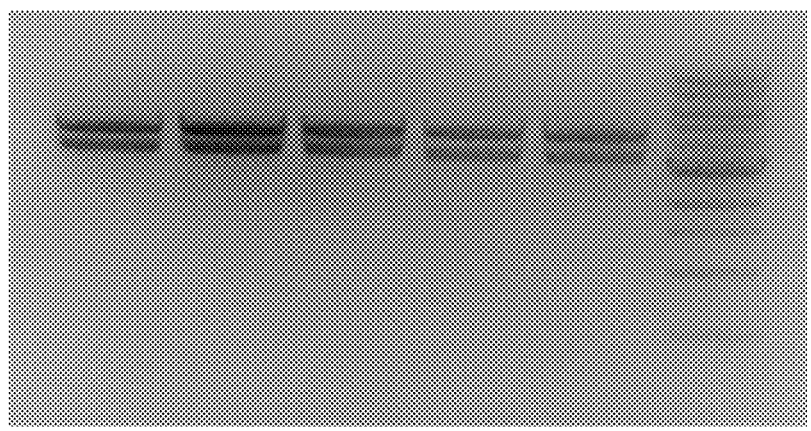

FIG. 14 shows proof of correct DNA assembly in Example 7. Purified plasmids from yellow colonies were checked by digestion with EcoRV and NdeI restriction enzymes. All plasmids show correct digestion pattern.

DETAILED DESCRIPTION

Systems

Figure 1:
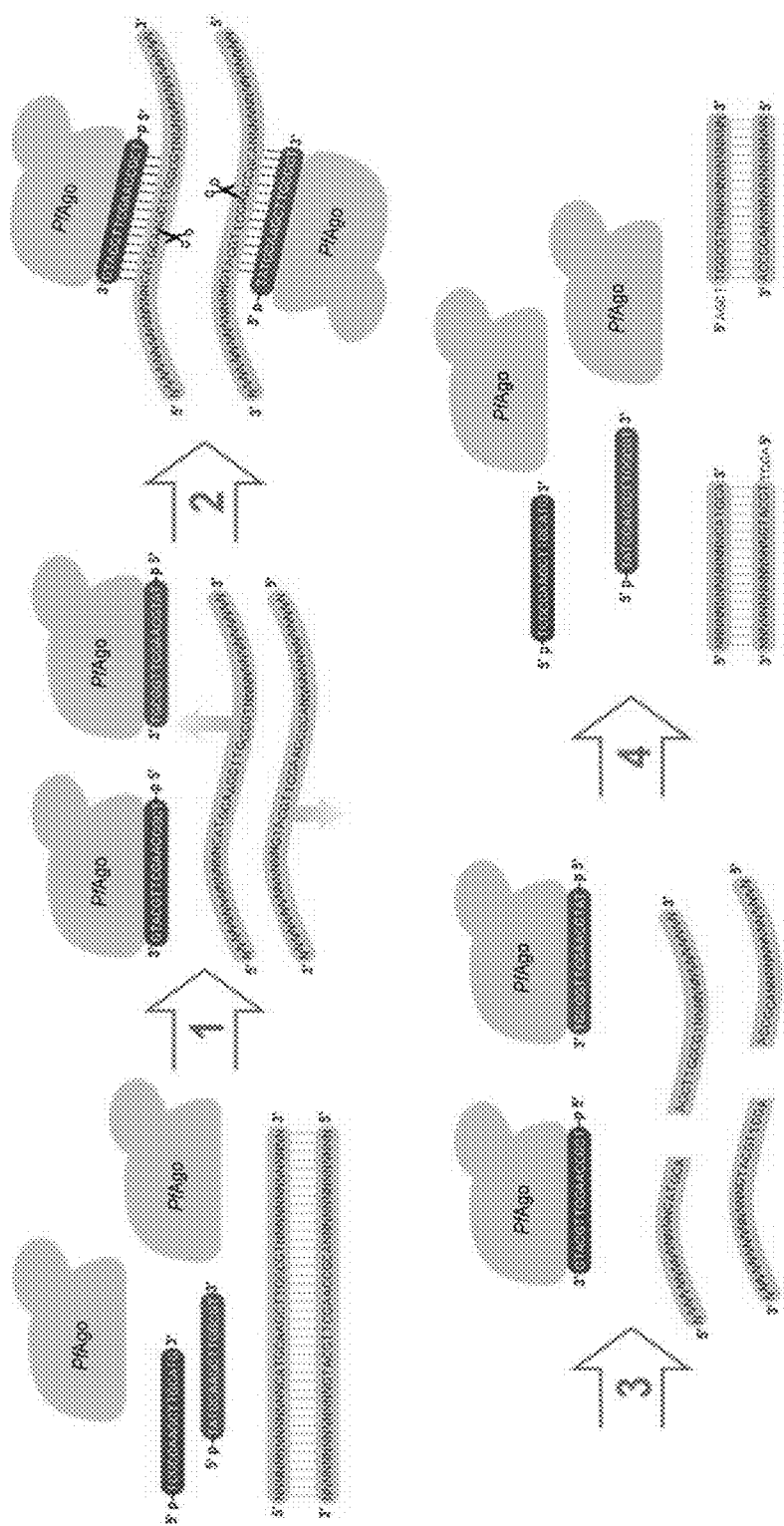
FIG. 1. Overview of the PfAgo/ARE platform. Step 1: by incubating the reaction mixture at high temperatures (87-98° C.), the dsDNA target is completely or partially denatured. PfAgo protein binds the 5'-phosphorylated ssDNA guides. Step 2: ssDNA guides bring PfAgo to their corresponding targets. Upon binding, PfAgo is able to cleave each target at specific position. Step 3: After each strand cleavage, PfAgo leaves its target DNA. Step 4: by decreasing the temperature, the two DNA strands re-anneal and dsDNA cleavage is complete. The following sequences are shown in FIG. 1.

A DNA-programmable nuclease system is disclosed that can be used to make a new class of AREs capable of recognizing and cleaving DNA sequences at virtually any arbitrary site and generating defined sticky ends of varying length or blunt ends. Two strands of DNA (circular or linear) can be separated by, for example, incubating the DNA samples at high temperatures. After the two strands of DNA are partially or completely separated (denatured), an Ago protein, such as PfAgo, can use one or more (e.g., two different) single-stranded DNA guides, targeting two strands of DNA at the desired locations, and cleave the strands in separate events. Once each strand of DNA is cleaved at the desired location, the two strands can re-anneal or hybridize to generate desired cleaved dsDNA (FIG. 1).

Systems, for example in vitro systems, are provided comprising one or more Ago proteins, e.g., a *Pyrococcus furiosus* Ago protein ("PfAgo"), and one or more single-stranded DNA guides.

In an embodiment, a PfAgo protein can be used in combination with one or more single-stranded guide sequences, e.g., 1, 2, 3, 4, 5, 6, 7, 8, 9, 10, 11, 12, 15, 20, 25, 30, or more guide sequences that target sense and/or anti-sense strands of target DNA. This system allows one or both target DNA strands to be nicked.

Aqo Protein

Prokaryotic Argonaute (Ago) proteins from *Pyrococcus furiosus, Thermococcus thioreducens* (WP_055429304), *Thermococcus onnurineus* (WP_012572468), *Thermococcus eurythermalis* (WP_050002102), *Methanocaldococcus bathoardescens* (WP_048201370), *Methanocaldococcus* sp. FS406-22 (WP_012979970), *Methanocaldococcus fervens* (WP_015791216), *Methanocaldococcus jannaschii* (WP_010870838), *Methanotorris formiscicus* (WP_052322764), *Ferroglobus placidus* (WP_012966655), *Thermogladius cellulolyticus* (WP_048163021), *Marinobacter* sp., *Thermus filiformis* (WP_038066338), *Thermus thermophilus* (WP_011229221), *Thermus* sp. NMX2.A1 (WP_038030409), *Thermus* sp. 2.9 (WP_039457454), *Thermus* sp. CCB_US3_U F1 (WP_014514637), *Thermus scotoductus* (WP_038044516), *Thermus arciformis* (SDF04754), *Thermus scotoductus, Thermosynechococcus* sp. NK55a (WP_041429921), *Thermosynechococcus elongates* (WP_011056792), *Thermus aquaticus*, and *Thermus parvatiensis* (WP_008631444) can be used in the methods described herein.

In an embodiment, an Ago protein has 25, 30, 40, 50, 60, 70, 80, 90, 95, 99 percent or more sequence identity to an *Pyrococcus furiosus* Ago protein. In an embodiment an Ago protein is from thermophilic or hyperthermic bacteria or archaea. Thermophilic bacteria or archaea have growths temperatures of about 40° C. to about 75° or more and an optimal growth temperature of about 60° C. Hyperthermic bacteria or archaea have growth temperatures of about 65° C. to 120° C. and an optimal growth temperature of about 80° C.

Ago proteins utilize small DNA or RNA guides to cleave single-stranded DNA targets. PfAgo protein from *Pyrococcus furiosus* is a DNA-guided nuclease (771 amino acids) (SEQ ID NO:66; see FIG. 9) that targets cognate DNA (10).

In an embodiment, a coding sequence encoding an Ago protein, e.g., PfAgo can be codon optimized for expression in certain host cells, such as prokaryotic or eukaryotic cells. Prokaryotic cells include, for example E. coli. Eukaryotic cells can be for example, yeast cells or mammalian cells such as human, mouse, rat, rabbit, dog, or non-human primate. Codon optimization is a process of modifying a nucleic acid sequence for enhanced expression in host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Different species can exhibit a bias for certain codons of an amino acid. Codon bias (differences in codon usage between organisms) can correlates with efficiency of translation of messenger RNA (mRNA). Therefore, Ago polynucleotides can be altered for optimal gene expression in a given organism based on codon optimization. Codon usage tables are known in the art. See Nakamura et al. "Codon usage tabulated from the international DNA sequence databases: status for the year 2000" Nucl. Acids Res. 28:292 (2000). Computer algorithms for codon optimizing a particular sequence for expression in a particular host cell are also available, e.g., Gene Forge (Aptagen; Jacobus, Pa.). In an embodiment, one or more codons (e.g. 1, 2, 3, 4, 5, 10, 15, 20, 25, 50, or more, or all codons) in a nucleotide sequence encoding an Ago protein correspond to the most frequently used codon for a particular amino acid in a host cell. In an embodiment, an Ago polynucleotide is codon optimized for expression in E. coli. SEQ ID NO:67 demonstrates a PfAgo polynucleotide that is optimized for expression in E. coli. See FIG. 9.

An Ago protein, such as PfAgo, can be present as a fusion protein and can comprise one or more additional heterologous functional domains (e.g. about or more than about 1, 2, 3, 4, 5, 6, 7, 8, 9, 10, or more domains in addition to Ago). An Ago fusion protein can comprise any additional protein sequence, and optionally a linker sequence between additional protein sequences. Examples of proteins that can be fused to Ago include, for example, tags or labels, reporter gene sequences, and proteins having one or more of the following activities: methylase activity, demethylase activity, transcription activation activity, transcription repression activity, transcription release factor activity, histone modification activity, RNA cleavage activity, nucleic acid binding activity, and helicase activity.

Examples of tags or labels include histidine (His) tags, V5 tags, FLAG tags, influenza hemagglutinin (HA) tags, Myc tags, VSV-G tags, and thioredoxin (Trx) tags. Examples of reporter genes include glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). Ago can be fused to an amino acid sequence encoding a protein or a fragment of a protein that bind DNA molecules or that bind to other cellular molecules, such as maltose binding protein (MBP), S-tag, Lex A DNA binding domain (DBD) fusions, GAL4 DNA binding domain fusions, and herpes simplex virus (HSV) BP16 protein fusions. In an embodiment, a tagged or labeled Ago can be used to identify the location of a target DNA sequence. For example, a single-stranded DNA guide having complementarity to a target DNA molecule can be used with a labeled Ago protein to identify a target DNA sequence.

A "DNA guide target sequence" is a sequence within target DNA to which a DNA guide sequence is designed to have complementarity, where hybridization between a target sequence of a target DNA molecule and a DNA guide sequence/Ago complex promotes the formation of an Ago complex (e.g., a complex of one or more DNA guides, one or more Ago proteins, and a target DNA molecule). Full complementarity between a DNA guide molecule and a DNA guide target sequence is not necessarily required, provided there is sufficient complementarity to cause hybridization and promote formation of an Ago complex.

Typically, in the context of an Ago system, formation of an Ago complex results in cleavage of the DNA target molecule within or near (e.g. within 1, 2, 3, 4, 5, 6, 7, 8, 9, 10 or more base pairs from) the DNA guide target sequence.

Single-Stranded DNA Guides

Systems can comprise one or more single-stranded DNA guides. One or more of the single-stranded DNA guides in a system can be 5'-phosphorylated. One or more DNA guides can target two strands of DNA (sense and antisense strand) at any desired locations, and cleave the strands in separate events. Once each strand of DNA is cleaved at the desired location, the two strands can re-anneal or hybridize to generate desired cleaved dsDNA FIG. 1.

A guide molecule is any single-stranded deoxyribonucleic acid molecule having sufficient complementarity with a target deoxyribonucleic acid molecule to hybridize with the target molecule. A guide molecule forms a complex with an Ago protein and directs sequence-specific binding of the guide molecule/Ago complex to the target DNA molecule. The degree of complementarity between a guide molecule and its corresponding target DNA molecule, when optimally aligned using a suitable alignment algorithm, is about 50%, 60%, 75%, 80%, 85%, 90%, 91%, 92%, 93%, 94%, 95%, 96%, 97%, 98%, 99%, or more. In an embodiment the complementarity is 100%. Optimal alignment can be determined with any suitable algorithm for aligning sequences, for example, Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, and ELAND (Illumina, San Diego, Calif.). A guide sequence can be about or more than 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 90, 100 or more nucleotides in length (or any range between about 9 and 100 nucleotides). A guide sequence can be less than about 100, 90, 80, 75, 60, 50, 45, 40, 35, 30, 29, 28, 27, 26, 25, 24, 23, 22, 21, 20, 19, 18, 17, 16, 15, 14, 13, 12, 11, or 10 nucleotides in length.

The ability of a guide molecule to direct sequence-specific binding of Ago to a target DNA molecule can be tested using any suitable assay. For example, cleavage of a target DNA molecule can be evaluated in vitro by contacting a test target molecule, Ago, one or more test guide molecules having homology to the test target molecule, and a control guide sequence different from the test guide sequence, and comparing binding and/or rate of cleavage of the target DNA molecule between the test guide and control guide sequence reactions.

A guide molecule can be selected or designed to target and hybridize to any target molecule at a DNA guide target sequence. DNA guide target sequences can be unique in the target DNA molecule or can occur at two or more locations with the target DNA molecule. In an embodiment, an Ago protein can be used in combination with one or more single-stranded DNA guide sequences, e.g., 1, 2, 3, 4, 5, 6, 7, 8, 9, 10, 11, 12, 15, 20, 25, 30, or more guide sequences that target sense and/or antisense strands of target DNA molecules. This system allows both target DNA strands of the double-stranded DNA molecule to be nicked. Alternatively, only one target DNA strand can be nicked.

In some embodiments, a guide molecule is designed to reduce the degree of secondary structure within the guide molecule. Secondary structure can be determined by any suitable polynucleotide folding algorithm including, for example mFold (Zuker and Stiegler (Nucleic Acids Res 9 (1981), 133-148)).

In an embodiment, the guide molecules are designed so that a first guide molecule hybridizes to a sense strand of a denatured or partially denatured DNA molecule and a second guide molecule hybridizes to an anti-sense strand of a denatured or partially denatured DNA molecule. The first and second guide molecules can have the same sequence or, more often, different sequences. The first and second guide molecules can be designed so that when the Ago protein cleaves the sense and antisense strand of the target DNA the target molecule has overlapping or sticky ends (ends of DNA that can hybridize to one another). In another embodiment, the guide molecules are designed so that when the Ago protein cleaves the sense and antisense strand of the target DNA, blunt ends are generated.

In an embodiment, the Ago protein, e.g., PfAgo protein, and the one or more single-stranded DNA guides do not occur together in nature. In an embodiment, single-stranded DNA guides are synthetic and do not occur in nature. In an embodiment the single-stranded DNA guides are not from *Pyrococcus furiosus* or *Thermus thermophilus*. In an embodiment the single-stranded DNA guides comprise one or more labels or tags.

A DNA guide molecule and Ago protein form a complex. The guide molecule provides target specificity to the complex by comprising a nucleotide sequence that is complementary to a sequence of a target DNA. The guide of the complex provides the site-specific activity. In other words, the Ago protein is guided to the target DNA molecule (e.g. a chromosomal sequence or an extrachromosomal sequence, e.g. an episomal sequence, a minicircle sequence, a mitochondrial sequence, a chloroplast sequence, etc.) by virtue of its association with at least the DNA guide molecule. The Ago protein cleaves target DNA. In some cases, the Ago is a naturally-occurring polypeptide. In other cases, the Ago is not a naturally-occurring polypeptide (e.g., a chimeric polypeptide or a naturally-occurring polypeptide that is modified by, e.g., amino acid mutation, deletion, insertion).

The one or more single-stranded DNA guides can be designed to leave sticky ends (i.e., overhanging ends) that can hybridize to each other once the one or more target portions are removed. Therefore, the ends shown below:

```
                              (SEQ ID NO: 68)
         5'-AGATAGCATTTA-3'

(SEQ ID NO: 69)
         5'-GCTAAT-3'

(SEQ ID NO: 70)
         3'-TCTATC-5'

(SEQ ID NO: 71)
         3'-GTAAATCGATTA-5'
```

Can hybridize as follows:

```
                              (SEQ ID NO: 72)
         5'-AGATAGCATTTAGCTAAT-3'

(SEQ ID NO: 75)
         3'-TCTATCGTAAATCGATTA-5'
```

Sticky ends can have overhangs of about 1, 2, 3, 4, 5, 6, 7, 8, 9, 10, 11, 12, 13, 14, 15, 20, 30, 40 or more nucleotides.

Alternatively, overhanging ends can be generated that do not have homology. In this case the non-homologous overhanging ends can be converted to blunt ends by blunting. Blunting is the elimination of incompatible 3' or 5' overhangs. Terminal unpaired nucleotides can be removed from DNA by using an enzyme with exonuclease activity, which hydrolyzes a terminal phosphodiester bond, thereby removing the overhang one base at a time. DNA fragments with 5' overhangs can be blunted by filling in a recessed 3' terminus with DNA polymerase in the presence of dNTPs. End removal or fill-in can be accomplished using a number of enzymes, including for example, DNA Polymerase I Large (Klenow) Fragment, T4 DNA Polymerase, or Mung Bean Nuclease. Once blunted, the double-stranded DNA is compatible with other blunt-ended double-stranded DNA. Blunt ends can be ligated with, for example, a ligase.

In an embodiment, a DNA guide molecule hybridizes to a DNA guide target sequence on a sense strand of a target molecule within about 1, 2, 3, 4, 5, 10, 15, 20, 30, 40, 50, 100, 200, 300, 400, 500, 1,000 nucleotides or more of where a DNA guide molecule hybridizes to a DNA guide target sequence on an anti-sense strand of the target DNA molecule (determined from prior to denaturation or partial denaturation of the target DNA molecule).

Target Molecules

A target deoxyribonucleotide molecule can be any prokaryotic, eukaryotic, or synthetic polynucleotide. A target molecule can comprise a sequence coding a gene product (e.g., a protein) or a non-coding sequence (e.g., a regulatory polynucleotide or a non-coding DNA).

A target DNA is a polynucleotide that comprises a target site or DNA guide target sequence. The terms target site or target sequence refer to a nucleic acid sequence present in a target DNA to which a DNA guide can hybridize. For example, the target site (or target sequence) 5'-GAG-CATATCGGCC-3' (SEQ ID NO:76) within a target DNA is targeted by (or is bound by, or hybridizes with, or is complementary to) the DNA sequence 3'-CTCGTATAGCCGG-5' (SEQ ID NO:77). Suitable DNA binding conditions include physiological conditions normally present in a cell. Other suitable DNA binding conditions are known in the art; see, e.g., Green & Sambrook, Molecular Cloning: A Laboratory Manual (Fourth Edition), Cold Spring Harbor Laboratory Press (2012).

Methods

An embodiment provides a method of creating an artificial restriction enzyme with distinct nucleotide sequence specificity. The method comprises providing an Ago protein and one or more single-stranded DNA guides, wherein the one or more single-stranded DNA guides comprise a distinct nucleotide sequence such that the one or more single-stranded DNA guides hybridize to a target DNA molecule. An artificial restriction enzyme with distinct nucleotide sequence specificity is an artificial restriction enzyme that has a specific or distinct nucleotide sequence that can hybridize to any desired target sequence. That is, the artificial restriction enzyme can be designed to hybridize to any target DNA molecule and to cleave the target DNA at any desired position. For example, if it is desired to cleave the target DNA molecule:

```
Target DNA
                                     (SEQ ID NO: 78)
3'-GGGCTAATACGGATTAGTCAAACTAA-5'
``` after the 18th nucleotide, then a DNA guide with distinct nucleotide sequence specificity can be designed as follows:

```
DNA Guide
                                     (SEQ ID NO: 79)
5'-TGCCTAATCAGTTTGA-3'

Target DNA
                                     (SEQ ID NO: 80)
3'-GGGCTAATACGGATTAGTCAAACTAA-5'
```

Such that when the DNA guide, target DNA, and Ago protein are brought into contact, the target DNA is cleaved after the underlined T.

An embodiment provides a method of site-specific modification of a target DNA molecule comprising: contacting the target DNA molecule with: (i) one or more single-stranded DNA guide molecules having complementarity to the target DNA molecule and (ii) an Ago protein.

Compositions and systems disclosed herein can be used in many different methods. In an embodiment, a method of cleaving one or more double-stranded DNA molecules is provided. The method can comprise denaturing (partially or entirely) one or more double-stranded DNA molecules into partially denatured double-stranded DNA molecules or first single-stranded DNA molecules (e.g., sense DNA molecules) and second single-stranded DNA molecules (e.g., anti-sense DNA molecules). DNA denaturation is the unwinding and separation of double-stranded deoxyribonucleic acid so that the double strands are separated into single-stranded strands or so that the double strands are partially separated into single-strands. Denaturation or partial denaturation can be accomplished through heating the molecules or through the use of chemicals such as formamide, urea, dimethyl sulfoxide, or high pH. When using heat to denature double-stranded DNA, the melting temperature ($T_m$) of the DNA is the temperature at which half of the DNA strands are in the random coil or single-stranded (ssDNA) state. $T_m$ depends on the length of the double-stranded DNA molecule and the specific nucleotide sequence of the molecule. The amount of strand separation, or melting, can be measured by the absorbance of the DNA solution at 260 nm. One of skill in the art can readily determine an optimal temperature to denature a double-stranded DNA molecule. In an embodiment, double-stranded DNA molecules are denatured at about 50, 60, 70, 80, 85, 86, 87, 88, 89, 90, 91, 92, 93, 94, 95, 96, 97, 98, 99, 100, 105, 110 or more degrees Celsius.

In an embodiment, double-stranded DNA molecules are considered denatured when about 30, 40, 50, 60, 70, 80, 90, 95, 99, or more of the DNA strands are in the random coil or single-stranded state. A partially denatured double-stranded DNA molecule can be a DNA molecule wherein about 30, 40, 50, 60, 70, 80, 90, 95, 99, or more of the DNA strands are in the random coil or single-stranded state. In an embodiment, double-stranded DNA molecules are considered denatured when 100% of the DNA strands are in the random coil or single-stranded state.

In an embodiment a double-stranded DNA molecule is considered denatured when about 30, 40, 50, 60, 70, 80, 90, 95, 99, or more of the complementary base pairs of the sense and anti-sense stand are not hydrogen bonded to one another. A partially denatured double-stranded DNA molecule can be a DNA molecule wherein about 30, 40, 50, 60, 70, 80, 90, 95, 99, or more of the complementary base pairs of the sense and anti-sense stand are not hydrogen bonded to one another.

In an embodiment, denaturation occurs in vitro.

Once denatured or partially denatured, the first single-stranded target DNA molecules and the second single-stranded target DNA molecules or partially denatured double-stranded DNA molecules can be contacted with (i) one or more single-stranded DNA guide molecules that can hybridize to the first single-stranded DNA molecules and the second single-stranded DNA molecules or to the partially denatured double-stranded DNA molecules and (ii) one or more Ago proteins, such as PfAgo protein. The molar ratio of DNA guide molecules to Ago protein can be about 1:1, 1:2, 1:3, 1:4, 1:5, 1:6, 1:7, 1:8, 1:9, 1:10, 1:15, 1:20, 1:25, 1:30, 1:35, 1:40, 1:50, 1:60, 1:75, 1:100, 2:1, 3:1, 4:1, 5:1, 6:1, 7:1, 8:1, 9:1, 10:1, 15:1, 20:1, 25:1, 30:1, 35:1, 40:1, 50:1, 60:1, 75:1, or 100:1. Optionally, the double-stranded target, one or more DNA guide molecules and an Ago protein can be contacted and then subjected to conditions to denature or partially denature the double-stranded DNA target.

The one or more single-stranded DNA guide molecules bind to the Ago protein and hybridize to the first and second single-stranded DNA molecules or partially denatured double-stranded DNA molecules. The Ago protein cleaves the target DNA molecules at a specific position, usually between the 10th and 11th nucleotide position of the single-stranded DNA guide. See, e.g. FIG. 4A. The target DNA can be cleaved at 1, 2, 3, 4, 5, 6, 7, 8, 9, 10, 15, 20 or more positions using one or more DNA guide molecules (e.g. about 1, 2, 3, 4, 5, 6, 7, 8, 9, 10, 11, 12, 13, 14, 15, 16, 17, 18, 19, 20, 30, 40, 50 or more). The first single-stranded DNA molecules and the second single-stranded DNA molecules or partially denatured double-stranded DNA can then be allowed to hybridize by, for example, lowering the temperature. Full complementarity between the first single-stranded DNA molecules and second single-stranded DNA molecules or the partially denatured double-stranded DNA is not necessarily required, provided there is sufficient complementarity to cause hybridization of the molecules to form a double-stranded helical DNA molecule.

Any nicks in the hybridized double-stranded DNA molecule can be ligated with a DNA ligase, such as T4 ligase. Purification steps can optionally be present at any step.

An embodiment provides a method of cleaving one or more target single-stranded DNA molecules. The method comprises contacting the target single-stranded DNA molecules with (i) one or more single-stranded DNA guide molecules that can hybridize to the target single-stranded DNA molecules and (ii) an Ago protein. The target single-stranded DNA molecule can be cleaved at 1, 2, 3, 4, 5, 6, 7, 8, 9, 10, 15, 20 or more positions using one or more guide molecules. Purification steps can optionally be present at any step.

An embodiment provides a method of removing one or more target portions from double-stranded DNA molecules. A target portion is a double-stranded unwanted portion of the double-stranded target DNA molecule. In an embodiment a target portion can be a portion or part of the double-stranded target DNA molecule between two cleavage sites on the sense and antisense strands. The method comprises denaturing double-stranded DNA molecules into first single-stranded DNA molecules and second single-stranded DNA molecules or partially denatured double-stranded DNA molecules. The first single-stranded DNA molecules and the second single-stranded DNA molecules or partially denatured double-stranded DNA molecules can be contacted with (i) one or more single-stranded DNA guides that can hybridize to the first single-stranded DNA molecules and to the second single-stranded DNA molecules or to the partially denatured double-stranded DNA molecules, and (ii) one or more Ago proteins, such as PfAgo protein. The Ago protein cleaves first single-stranded DNA molecules and the second single-stranded DNA molecules or the partially denatured double stranded DNA molecules on the sense strand and on the antisense strand. The first single-stranded DNA molecules and second single-stranded DNA molecules can be allowed to hybridize such that one or more target portions are removed from the target DNA molecule. Alternatively, when the partially denatured double-stranded DNA molecules are cleaved, one or more target portions of the double-stranded DNA molecules are removed such that when the partially denatured double-stranded DNA molecules hybridize, one or more target portions of the double-stranded DNA molecules are removed. Any nicks can be ligated with a DNA ligase. Purification steps can optionally be present at any step.

The one or more DNA guides can be designed such that one or more portions of the double-stranded DNA are removed when the first and second single-stranded DNA molecules or the partially denatured double-stranded DNA molecules hybridize.

Hybridization and/or ligation of DNA molecules in methods disclosed herein can occur under conditions that are permissive for nonhomologous end joining or homology-directed repair. Using these techniques, target DNA can be cleaved and rejoined to produce a modified DNA molecule with a different nucleotide sequence than the original target DNA molecule.

An embodiment provides a method of removing one or more target portions from single-stranded DNA molecules. Single-stranded DNA molecules can be contacted with one or more single-stranded DNA guides that can hybridize to the single-stranded DNA molecules and an Ago protein, such as PfAgo. The single-stranded DNA molecules are cleaved. The single-stranded DNA molecules can be ligated together with, for example, a ligase. One or more target portions of the single-stranded DNA molecules are thereby removed. Purification steps can optionally be present at any step.

An embodiment provides a method of inserting one or more target double-stranded DNA molecules or one or more target single-stranded DNA molecules into recipient double-stranded DNA molecules. The method comprises denaturing the recipient double-stranded DNA molecules into first single-stranded recipient DNA molecules and second single-stranded recipient DNA molecules or partially denatured recipient double-stranded DNA molecules. The first recipient single-stranded DNA molecules and the second single-stranded recipient DNA molecules or the partially denatured recipient double-stranded DNA molecules are contacted with one or more single-stranded DNA guides that can hybridize to the first single-stranded recipient DNA molecules and to the second single-stranded recipient DNA molecules, or the partially denatured recipient double-stranded DNA molecules, and an Ago protein, such as PfAgo. The DNA guides hybridize to the first single-stranded recipient DNA molecules and to the recipient second single-stranded DNA molecules or to the partially denatured recipient double-stranded DNA molecules. The Ago protein cleaves the first single-stranded recipient DNA molecules and the second single-stranded recipient DNA molecules or the sense and anti-sense strands of the partially denatured recipient double-stranded DNA molecules. The first single-stranded recipient DNA molecules and the second single-stranded recipient DNA molecules or partially denatured recipient double-stranded DNA molecules can be purified. The first single-stranded recipient DNA molecules and the second single-stranded recipient DNA molecules or the partially denatured recipient double-stranded DNA molecules can be dephosphorylated with, e.g., rSAP.

The target DNA molecules can be single-stranded or double-stranded. Double-stranded target DNA molecules can be denatured or partially denatured and contacted with one or more single-stranded DNA guides that can hybridize to the target DNA molecules and an Ago protein to generate complementary ends to the first single-stranded recipient DNA molecules and to the second single-stranded recipient DNA molecules or to the partially denatured recipient double-stranded DNA molecules. The target DNA molecules can hybridize to make double-stranded DNA molecules with complementary ends to the recipient DNA. The target double-stranded DNA molecules can be purified. Alternatively, the target double-stranded DNA molecules can be provided with complementary ends to the first single-stranded recipient DNA molecules and to the second single-stranded recipient DNA molecules or to the partially denatured recipient double-stranded DNA molecules. The first single-stranded recipient DNA molecules and the second single-stranded recipient DNA molecules or the partially denatured recipient double-stranded DNA molecules are allowed to hybridize and are contacted with the double-stranded target DNA molecules such that the double-stranded target DNA molecules or a portion of the double-stranded target DNA molecules are inserted into the recipient DNA molecules. A ligase can be used to ligate any nicks in the final double-stranded DNA molecule. Purification steps can optionally be present at any step.

An embodiment provides a method of inserting one or more target single-stranded DNA molecules into recipient single-stranded DNA molecules. The method comprises contacting the recipient single-stranded DNA molecules with one or more single-stranded DNA guides that can hybridize to the first single-stranded recipient DNA molecules and Ago protein, such as PfAgo protein so that the recipient single-stranded DNA molecules are cleaved. The recipient single-stranded DNA molecules can be dephosphorylated with, e.g., shrimp alkaline phosphatase (rSAP).

One or more target single-stranded DNA molecules are contacted with the cleaved single-stranded DNA molecules. The one or more target single-stranded DNA molecules are inserted into the recipient single-stranded DNA molecules. Purification steps can optionally be present at any step. A ligase can be used to ligate any nicks in the final DNA construct. Purification steps can optionally be present at any step.

An embodiment provides methods of creating nicks in double-stranded DNA molecules. The method can comprise denaturing (partially or entirely) one or more double-stranded DNA molecules into first single-stranded DNA molecules (e.g., sense DNA molecules) and second single-stranded DNA molecules (e.g., anti-sense DNA molecules) or partially denatured double-stranded DNA molecules. The first single-stranded target DNA molecules and the second single-stranded target DNA molecules or the partially denatured double-stranded DNA molecules can be contacted with (i) one or more single-stranded DNA guide molecules that can hybridize to the first single-stranded DNA molecules and to the second single-stranded DNA molecules and (ii) an Ago protein, such as PfAgo protein. The one or more single-stranded DNA guide molecules hybridize to the first and second single-stranded DNA molecules or to the partially denatured double-stranded DNA molecules. The Ago protein associated with the DNA guide molecules cleaves the one or more first and second single-stranded DNA molecules or the partially denatured double-stranded DNA molecules. The first single-stranded DNA molecules and the second single-stranded DNA molecules or the partially denatured double-stranded DNA molecules can then be allowed to hybridize by, for example, lowering the temperature. Nicks are created in the sense and anti-sense strand of the target DNA molecule. In an embodiment, one or more DNA guides can be used to create one or more nicks in only the sense or only the anti-sense strand of the target DNA molecules.

An embodiment provides methods for using one or more elements of an Ago system. The Ago proteins and single-stranded DNA guides provide an effective means for modifying one or more target polynucleotides. The systems have a wide variety of utility including modifying (e.g., deleting, inserting, translocating, inactivating, activating) a target polynucleotide. As such systems have a broad spectrum of applications in, e.g., molecular cloning, in vitro DNA assembly, construction of DNA libraries, DNA computing, DNA storage, etc.

For example, compositions and methods described herein can be used in methods of DNA fingerprinting or DNA mapping. One or more double-stranded DNA molecules can be denatured into first single-stranded DNA molecules and second single-stranded DNA molecules or partially denatured double-stranded DNA molecules. Optionally, the one or more double-stranded DNA molecules can be amplified prior to denaturation. The first single-stranded DNA molecules and the second single-stranded DNA molecules or partially denatured double-stranded DNA molecules can be contacted with (i) one or more single-stranded DNA guide molecules that can hybridize to the first single-stranded DNA molecules and the second single-stranded DNA molecules or to the partially denatured double-stranded DNA molecules and (ii) an Ago protein, wherein the one or more double-stranded DNA molecules are cleaved. The first single-stranded DNA molecules and the second single-stranded DNA molecules or the partially denatured double-stranded DNA molecules can be hybridized to form double-stranded DNA molecule fragments. The double-stranded DNA molecule fragments can be separated by for example, size or by sequence, and analyzed. In an embodiment the double-stranded DNA molecule fragments are labeled or dyed.

In an embodiment agarose gel electrophoresis is used to resolve or separate the double-stranded DNA fragments by size. Unique and distinguishable patterns of DNA fragment sizes can be used to, for example, determine the relatedness of DNA samples.

In an embodiment, the double-stranded DNA fragments are sorted according to size and incubated with probes that bind to particular DNA sequences, for example, in the case of mammalian DNA, minisatellites. Multiple types of probes (e.g., 5, 10, 15, 10, 20, 30, 40, 50 or more probes) that recognize different particular DNA sequences (e.g., minisatellites) can be used simultaneously. Labeled fragments can be analyzed. In an example, DNA probe labeled fragments from two samples are compared. If the fragments are all the same size, then the two samples can be concluded to have originated from the same individual or DNA sample.

Compositions and systems described herein can also be used in DNA assembly. Since the characterization of restriction enzymes and the first construction of recombinant DNA using restriction digestion and DNA ligation (15), DNA assembly has become one of the most important tools for applications in biotechnology and synthetic biology. Using various DNA assembly methods, scientists have been able to construct complex metabolic pathways and genetic circuits from registries of modular components. Although various DNA assembly methods have been developed over the years, DNA assembly is still one of the limiting technologies in advancing synthetic biology (16). DNA assembly can be used to construct DNA parts into genes, multiple genes into pathways, and ultimately multiple pathways into genome. Currently, DNA assembly technologies can be divided into three categories, which are, (i) restriction enzyme based assembly, (ii) long homologous overlap-based assembly, and (iii) bridging oligo assembly (17). Although, each of the aforementioned technologies possesses its own advantages, construction of complex DNA constructs usually requires using several technologies in tandem. Here, we propose a new DNA assembly technology based on Argonaute-based artificial restriction enzymes which can potentially overcome the drawbacks of current DNA assembly technologies and be used for combinatorial construction of DNA parts in a pre-determined order fashion using a parallel reaction.

One of the common bottlenecks of native restriction enzyme based DNA assembly technologies is that most commercially available restriction enzymes (i.e. type II restriction enzymes) have short sequence recognition sites (4-8 nt). As a result, construction of large DNA constructs using these technologies becomes a challenging process since all DNA parts are required to be free of restriction enzyme recognition sites. On the other hand, most native restriction enzymes produce short sticky ends (usually 4 nt) which potentially produces problems when multiple DNA fragments are required to be assembled in a parallel (one pot) reaction. Unlike most native restriction enzymes, Argonaute-based AREs offer unprecedented target specificity as their recognition site could differ from 14 bp to over 25 bp based on the generated sticky ends size. This highly specific target recognition site offers a great advantage over native restriction enzymes since there is a really low probability that these targets occur in other DNA fragments. Furthermore, Argonaute-based AREs are able to produce arbitrary sticky ends which could efficiently be optimized to assemble large DNA constructs as there is potentially no limit in the number of orthogonal specific sticky ends.

DNA assembly using Argonaute-based AREs can happen through ligation dependent or ligation-independent processes. The first step for this DNA assembly technology is to use Ago-based AREs to produce desired sticky ends with desired size at the ends of dsDNA fragments. Since Ago-based AREs offer high target specificity, all DNA fragments could be digested in a one-pot or parallel reaction. Once the desired sticky ends are generated, the fragments can be assembled together with help of DNA hybridization using the complementary sticky ends on each fragment. For ligation dependent process, depending on sticky ends size, the optimum ligation temperature and optimum DNA ligase enzyme can be characterized. In the case of ligation-independent method, the digested DNA fragments could be assembled together using in vitro recombination or in vivo assembly similar to existing DNA assembly techniques (18, 19, 20). A schematic representation Ago-based DNA assembly is shown in FIG. 11.

In an embodiment a method of assembling two or more double-stranded DNA molecules into one or more larger double-stranded DNA molecules is provided.

In a single reaction, two or more double-stranded DNA molecules can be denatured or partially denatured. The denatured or partially denatured DNA molecules can be contacted with two or more single stranded guides and an Ago protein, wherein the two or more single-stranded guides are designed to generate specific overhanging ends on the resulting two or more double-stranded DNA molecules. The two or more denatured or partially denatured DNA molecules are cleaved by the Ago protein. The cleaved denatured or partially denatured DNA molecules are allowed to hybridize to generate two or more double-stranded DNA molecules with specific overhanging ends. At the same time or sequentially in time the cleaved DNA molecules are allowed to hybridize to generate two or more double-stranded DNA molecules with specific overhanging ends, the two or more double-stranded DNA molecules with specific overhanging ends are allowed to hybridize via the specific overhanging ends such that the two or more double-stranded DNA molecules are assembled into one or more larger double-stranded DNA molecules.

Alternatively, the two or more double-stranded DNA molecules with specific overhanging ends can be formed in separate reactions. That is, each of the two or more double-stranded DNA molecules with specific overhanging ends are generated separately and then combined. For example, in separate reactions (e.g., separate containers) two or more double-stranded DNA molecules are denatured or partially denatured. Each of the denatured or partially denatured DNA molecules are contacted with two or more single-stranded guides and an Ago protein, wherein the two or more single-stranded guides are designed to generate specific overhanging ends on the resulting double-stranded DNA molecules. The denatured or partially denatured DNA molecules are cleaved. The denatured or partially denatured DNA molecules are allowed to hybridize to generate double-stranded DNA molecules with specific overhanging ends. The two or more double-stranded DNA molecules with specific overhanging ends are combined. The two or more double-stranded DNA molecules with specific overhanging ends are allowed to hybridize via the specific overhanging ends such that the two or more double-stranded DNA molecules are assembled into one or more larger double-stranded DNA molecules.

The two or more double-stranded DNA molecules can be assembled into one or more larger double-stranded DNA molecules with ligation dependent or ligation-independent processes.

An Ago based system for generating AREs with virtually any sequence specificity and defined sticky ends of varying length have been established and demonstrated their applications in DNA fingerprinting and DNA cloning. Due to the unprecedented simplicity, programmability, generality, versatility, and multiplexing ability (a single protein plus DNA guides for targeting any one or more sites) as well as accessibility (easy high-level purification of an Ago protein and inexpensive synthesis of short DNA guides), Ago/AREs will become a powerful and indispensable tool in all restriction enzyme or broadly speaking, nuclease enabled basic and applied biological research and medicine.

Kits

In an embodiment kits are provided containing any one or more of the compositions disclosed above. A kit can comprise one or more Ago proteins, for example, PfAgo, one or more single-stranded DNA guides, one or more ligases, and instructions for using the kit. In an embodiment, the kit can be provided with an order form for DNA guides having specific nucleotide sequences so that the end user can order specific DNA guides to be delivered with their kit. In an embodiment, an end user can order specific DNA guides and kits using a computer that provides an interface with the end user for specific design of DNA guides and ordering of kits. Elements can be provided individually or in combinations, and may be provided in any suitable container, such as a vial, a bottle, or a tube.

In an embodiment, a kit comprises one or more reagents for use in a method utilizing one or more of the elements described herein. Reagents can be provided in any suitable container. For example, a kit may provide one or more reaction or storage buffers. Reagents can be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, Ago reaction buffer (20 mM HEPES pH 7.50, 250 mM NaCl, 0.5 mM $MnCl_2$), and combinations thereof. In some embodiments, the buffer is alkaline. In some embodiments, the buffer has a pH from about 7 to about 10.

As used herein, the singular forms "a," "an," and "the" include plural referents unless the context clearly dictates otherwise. For example, reference to a "DNA molecule" means one or more DNA molecules. The word "or" is intended to include "and" unless the context clearly indicates otherwise. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Unless otherwise explained, all technical and scientific terms used herein have the same meaning as commonly understood by one of ordinary skill in the art to which a disclosed disclosure belongs. "Comprising" means "including"; hence, "comprising A or B" means "including A" or "including B" or "including A and B." All references cited herein are incorporated by reference. Any of the terms "comprising", "consisting essentially of" and "consisting of" may be replaced with either of the other two terms. The disclosure may be further understood by the following non-limiting examples. All references cited herein are hereby incorporated by reference to the extent not inconsistent with the disclosure herewith. Although the description herein contains many specificities, these should not be construed as limiting the scope of the disclosure but as merely providing illustrations of some of the presently preferred embodiments of the disclosure. For example, the scope of the disclosure should be determined by the appended aspects and their equivalents, rather than by the examples given.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

When a Markush group or other grouping is used herein, all individual members of the group and all combinations and subcombinations possible of the group are intended to be individually included in the disclosure.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

Complement or complementary sequence means a sequence of nucleotides that forms a hydrogen-bonded duplex with another sequence of nucleotides according to Watson-Crick base-pairing rules. For example, the complementary base sequence for 5'-AAGGCT-3' (SEQ ID NO:81) is 3'-TTCCGA-5' (SEQ ID NO:82).

"Complementarity" refers to the ability of a nucleic acid molecule to form hydrogen bond(s) with another nucleic acid sequence by either traditional Watson-Crick or other non-traditional types. A percent complementarity indicates the percentage of residues in a nucleic acid molecule that can form hydrogen bonds (e.g., Watson-Crick base pairing) with a second nucleic acid molecule (e.g., 5, 6, 7, 8, 9, 10 out of 10 being 50%, 60%, 70%, 80%, 90%, and 100% complementary). "Perfectly complementary" or "perfect complementarity" means that all the contiguous residues of a nucleic acid molecule (e.g., a sense strand) will hydrogen bond with the same number of contiguous residues in a second nucleic acid molecule (e.g., an antisense strand). "Substantially complementary" or "substantial complementarity" refers to a degree of complementarity that is at least about 60%, 65%, 70%, 75%, 80%, 85%, 90%, 95%, 96%, 97%, 98%, 99%, or more over a region of 8, 9, 10, 11, 12, 13, 14, 15, 16, 17, 18, 19, 20, 21, 22, 23, 24, 25, 30, 35, 40, 45, 50, 60, 70, 80, 90, 100, 200, 300, 400, 500, 600, 700, 800, 900, 1,000, or more nucleotides, or refers to two nucleic acid molecules that hybridize under stringent conditions.

"Stringent conditions" for hybridization are conditions under which a nucleic acid having complementarity to a target sequence predominantly hybridizes with the target sequence, and does not substantially hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry and Molecular Biology-Hybridization with Nucleic Acid Probes Part 1, Second Chapter "Overview of principles of hybridization and the strategy of nucleic acid probe assay", Elsevier, N.Y.

Hybridization is the establishment of a non-covalent, sequence-specific interaction between complementary strands of nucleic acids into a single complex to form a DNA duplex. Deoxyribonucleotides will bind to their complement under normal conditions, so two complementary strands will bind to each other readily. 100% complementarity is not necessary to achieve hybridization. In an embodiment the first and second single-stranded DNA molecules; or double-stranded DNA; or DNA guide and DNA target molecule; or sticky ends of DNA molecules have about 60, 70, 80, 90, 95, 96, 97, 98, 99, or more complementarity (including 100% complementarity). A nucleic acid molecule capable of hybridizing with a target nucleic acid molecule is referred to as the "complement" of the given target nucleic acid molecule.

A polypeptide that is functionally equivalent to a specifically exemplified Ago polypeptide is a polypeptide that has been modified by single or multiple amino acid substitutions, by addition and/or deletion of amino acids, or where one or more amino acids have been chemically modified, but which nevertheless retains the activity of an Ago protein. Functionally equivalent polynucleotide molecules are those that encode Ago polypeptides having substantially the same biological activity as a specifically exemplified Ago protein.

Isolated means altered by the hand of man from the natural state. If an "isolated" composition or substance occurs in nature, it has been changed or removed from its original environment, or both. For example, a polynucleotide or a polypeptide naturally present in a living animal is not isolated, but the same polynucleotide or polypeptide separated from the coexisting materials of its natural state is isolated. Ago proteins and DNA guide molecules described herein can be isolated.

The terms "polynucleotide", "nucleotide", "nucleotide sequence", "nucleic acid", and "oligonucleotide" are used interchangeably. They refer to a polymeric form of nucleotides of any length, either deoxyribonucleotides or ribonucleotides, or analogs thereof. Polynucleotides can have any three dimensional structure, and can perform any function, known or unknown. Examples of polynucleotides include DNA molecules, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide can comprise one or more modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component.

A synthetic DNA molecule is a DNA molecule that does not occur in nature and can be, for example, artificial, man-made, a modified version of a gene, or a modified non-coding DNA.

The terms "non-naturally occurring," "engineered," "synthetic," or "recombinant" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

EXAMPLES

Example 1

PfAgo Expression and Purification

A strep(II)-tagged (N-terminal) codon-optimized version of PfAgo gene was ordered from GeneScript (Piscataway, N.J.). The codon-optimized gene was cloned into pET28a plasmid to yield the expression plasmid pHZ-PfAgo. The expression plasmid was transformed into *Escherichia coli* KRX (Promega) according to manufacturer's protocol. The strain was cultivated overnight at 37° C. in LB medium supplemented with 0.4% (w/v) glucose and 50 µg/ml kanamycin. Following overnight incubation, the culture was centrifuged at 3220×g for 5 min and the supernatant was removed. Cell pellets were resuspended in Terrific Broth containing 50 µg/ml kanamycin and incubated at 37° C. until the $OD_{600}$ of 1.2-1.5 was reached. The culture was cold shocked by incubation in ice bath for 15 min and protein expression was induced by addition of isopropyl β-D-1-thiogalactopyranoside (IPTG) and L-rhamnose to final concentrations of 1 mM and 0.1% (w/v), respectively. Expression was continued by incubation at 30° C. for 20 h. Purification was performed using previously mentioned protocol (10) with minor modification in the sonication step (twenty 30 sec pulses at 30% power with 30 sec pause between pulses). The purified protein was stored in storage buffer (20 mM Tris-HCl, pH 8.0, 300 mM NaCl, 0.5 mM $MnCl_2$, 15% (v/v) glycerol) and the aliquots were stored at −80° C.

Example 2

Restriction Digestion Using PfAgo/AREs and Native Restriction Enzymes

PfAgo is able to use short DNA guides (e.g., about larger than 15 nt) to cleave a ssDNA target. The DNA guides can be 5'-phosphorylated. A PfAgo gene was codon-optimized for high-level expression in *E. coli*. 16 nt DNA guides were used for all the experiments. See Table 2. Like its other prokaryotic counterpart, ttAgo (11), PfAgo is believed to cleave its ssDNA target between 10 and 11 nt position of its ssDNA guide (FIG. 4A). To investigate specific cleavage by PfAgo, linearized pUC19 plasmid (linearized by NdeI) was cleaved using two DNA guides that are expected to generate HindIII sticky ends. After cleavage by PfAgo using HindIII guides, the cleavage product was purified and cleavage ends were filled using Klenow fragment polymerase. The resulting fragment was ligated to itself by blunt-end ligation and 40 assembled plasmids were sent for DNA sequencing for cleavage site analysis. Out of the 40 plasmids, 39 were correctly assembled, and 38 of the plasmids showed cleavage at the expected location (FIG. 4B). This high cleavage specificity of PfAgo makes generation of defined sticky ends possible.

To determine PfAgo activity in cleaving dsDNA target, linear pUC19 plasmid (linearized with XmnI) was cleaved using different concentrations of PfAgo protein to generate EcoRI sticky ends. PfAgo cleaved 1 µg of linear pUC19 plasmid in less than 10 minutes at 95° C. when more than 3.75 µmol of the protein was used (FIG. 5A). In addition, >100 nmol protein (sufficient for >25,000 reactions) was readily purified from 1 liter of *E. coli* culture and PfAgo is known to be a multiple-turnover enzyme (10). Therefore, PfAgo is a highly active and readily available protein for practical applications. To investigate whether PfAgo is able to cleave methylated DNA target, linear pUC19 plasmid (linearized with BsaI) was mixed with PfAgo and a set of DNA guides targeting an MboI restriction site on the plasmid. MboI recognizes GATC as its target sequence but is not able to cleave DNA when the target is methylated (5). PfAgo was able to cleave the methylated DNA target (FIG. 5B), demonstrating that PfAgo based AREs (PfAgo/AREs thereafter) are not sensitive to DNA methylation.

Materials and Methods.

For all PfAgo digestions (unless noted otherwise), the same reaction buffer (20 mM HEPES pH 7.50, 250 mM NaCl, 0.5 mM $MnCl_2$) was used. PfAgo, ssDNA guides, and target dsDNA were mixed together in the reaction buffer and incubated at high temperatures (87 to 98° C.). Following high temperature incubation, the samples were cooled down by slowly lowering the temperature with the rate of 0.1° C./s until 10° C. was reached. For all digestion reactions, the molar ratio of overall DNA guides to PfAgo was kept higher than 10:1 and all guides were mixed in equimolar ratios with respect to each other (unless noted otherwise). For all native restriction enzymes, the reactions were performed according to manufacturer's protocols. HindIII-HF, EcoRI-HF, XbaI, NdeI, AvrII, BamHI-HF, Bsu36I, BsaI-HF, MboI, and XmnI restriction enzymes were ordered from New England Biolabs (Ipswich, Mass.). For PCR cloning experiments, Fast-Digest PfoI and BamHI enzymes were purchased from Thermo Fisher Scientific (Waltham, Mass.). rSAP, DNA polymerase I, Klenow fragment, 1 kb and 100 bp DNA ladders were purchased from New England Biolabs.

Example 3

PCR Cloning Using PfAgo/AREs

To investigate whether PfAgo AREs can be used for routine cloning of gene products amplified by polymerase chain reaction (PCR), xylE was selected from *Pseudomonas putida* (~1 kb in size) (12) and the Cas9 gene from *Streptococcus pyogenes* (~4 kb in size) (13) as well as the commonly used plasmid pUC19 as targets. For the first experiment, pUC19 plasmid was linearized using either XbaI, EcoRI, or HindIII and then dephosphorylated by shrimp alkaline phosphatase (rSAP). Each of the aforementioned genes was PCR amplified using primers to add 16 bp sequence of DNA corresponding to XbaI, EcoRI, or HindIII sites of pUC19 to each end and the amplified PCR product was digested with PfAgo using two DNA guides to generate sticky ends of the corresponding restriction enzyme on each end. The digested fragment was then ligated into the pUC19 backbone (FIG. 2A) and the assembled plasmids were analyzed by restriction digestion using the same restriction enzyme. More than 80% of the assembled plasmids showed the correct digestion pattern (FIG. 2B and FIG. 6). Such efficiency was comparable to native restriction enzymes for the same experiment (data not shown).

It is known that XbaI, EcoRI, and HindIII all produce 5' sticky ends with 4 nt. To investigate whether sticky ends of other lengths can be generated by the PfAgo AREs, the pUC19 plasmid was digested with either NdeI or PfoI and then dephosphorylated with rSAP. NdeI generates 5' sticky ends with 2 nt while PfoI generates 5' sticky ends with 5 nt. The xylE and Cas9 genes were PCR amplified with primers containing additional sequences corresponding to NdeI or PfoI sites on pUC19. The PCR products were then digested with PfAgo using NdeI or PfoI DNA guides. The digested PCR products were ligated into the digested and dephosphorylated vector backbone and the assembled plasmids were analyzed by restriction digestion with appropriate restriction enzymes. In overall, more than 80% of the plasmids showed the correct digestion pattern, indicating that PfAgo AREs can be used to generate arbitrary sticky ends (FIG. 2B).

Next, we explored whether plasmid vector and PCR products can both be digested with PfAgo using the same set of guides. pUC19 plasmid was first incubated with PfAgo using EcoRI guides. PfAgo was not able to cleave the negatively supercoiled pUC19 plasmid using EcoRI guides. This result suggests that even at high temperatures (90-100° C.) in PfAgo reaction buffer, the pUC19 plasmid strands could not be separated from each other at the EcoRI site to make the strands available for PfAgo cleavage. To overcome this problem, another DNA guide (pUC19-g7) was added to the reaction mixture. pUC19-g7 targets a region on the plasmid which has ~29% GC content (including a 20 bp flanking sequence on each side) (FIG. 2C). Due to the fact that strand separation is more likely to occur at low GC content regions, PfAgo would be able to generate a nick on the supercoiled plasmid at these sites. Once the nick is generated, the two strands would be partially or completely separated and PfAgo would be able to cleave the nicked plasmid at any desired location. As expected, pUC19 could be cleaved by PfAgo at EcoRI site using the additional guide (FIG. 2D).

Using the aforementioned strategy, both pUC19 and the PCR products were digested with PfAgo with a combination of DNA guides (4 in total) corresponding to different sets of restriction enzyme cut sites including EcoRI and HindIII, BamHI and PfoI, EcoRI and NdeI, and XbaI and NdeI. The assembled plasmids were analyzed by restriction digestion using the appropriate restriction enzyme set. In overall, more than 60% of the colonies showed the correct color (i.e. white) in a blue/white screening and more than 80% of the checked plasmids showed the correct assembly (FIG. 7). These results indicate that PfAgo can be used as a single enzyme to target a plasmid and PCR products at desired locations and can replace the use of multiple restriction enzymes.

To demonstrate the versatility of this PfAgo/ARE platform, both pUC19 and PCR products were digested at positions that no known restriction enzyme is able to cleave using two sets of DNA guides. Because no restriction enzyme is known to target these sites, the assembled plasmids were analyzed by PfAgo/ARE digestion using the same set of guides used for cloning (FIG. 2E). In overall, more than 70% of the colonies showed the correct color (i.e. white) in a blue/white screening and more than 80% of the checked plasmids showed the correct digestion pattern. Taken together, these results demonstrate that PfAgo/AREs can not only target the DNA regions that commercially available restriction enzymes can cleave, but also offer striking flexibility: DNA fragments can virtually be cleaved at any desired location and assembled together using appropriate sticky ends.

Materials and Methods

PCR Products Digestion with PfAgo

The xylE and cas9 genes were PCR amplified using the appropriate primers mentioned in Table 1. PCR reactions were performed by Q5 Hot Start DNA Polymerase (New England Biolabs) according to manufacturer's protocol. The PCR products were purified by agarose gel extraction using ZYMOCLEAN™ Gel DNA recovery Kit (Zymo Research). Purified PCR products were digested with PfAgo AREs. For either xylE or cas9, between 500 ng to 1 µg of the purified PCR product was digested in a 50 µl reaction containing PfAgo with the final concentration of ~0.2 µM. For all digestion reactions, the molar ratio of overall DNA guides to PfAgo was kept higher than 10:1. The reaction mixture was incubated at 95° C. for 10 min followed by slow cooling. The digested PCR products were purified using QIAQUICK® PCR purification kit (QIAGEN). Purified products were ligated into the corresponding digested backbones using T4 DNA ligase (New England Biolabs). For cas9 ligation, the ligation mixture was incubated overnight at 16° C. For xylE ligation, the ligation mixture was incubated at room temperature for 15 min. After ligation, all the reaction mixtures were transformed into NEB5α competent *E. coli* (New England Biolabs) according to manufacturer's protocol. pUC19 digestion with PfAgo/AREs For all pUC19 plasmid digestions, pUC19-g7 was added to the reaction mixture. For all cloning experiments with the vector digested by PfAgo/AREs, ~1 µg of pUC19 plasmid was digested in a 50 µl reaction containing PfAgo with the final concentration of ~0.2 µM. The ratio of pUC19-g7 to all other guides was kept at 1:2 and the molar ratio of overall DNA guides to PfAgo was kept higher than 10:1. The reaction mixtures were incubated at 95° C. for 15 min followed by slow cooling. Digested vectors were purified by agarose gel extraction and purification using ZYMOCLEAN™ Gel DNA recovery Kit. Analysis of correct plasmid assembly using PfAgo/AREs For digestion analysis of the plasmids assembled in random target cloning, between 700 ng to 1 µg of the assembled plasmids were mixed in the reaction buffer supplemented with 5% (v/v) DMSO and PfAgo with the final concentration of 0.2 µM. The ratio of pUC19-g7 to all other guides was kept at 1:2 and the molar ratio of overall DNA guides to PfAgo was kept higher than 10:1. The reaction mixtures were incubated at 87° C. for 30 min followed by incubation at 95° C. for 10 min. The samples were cooled down slowly until 10° C. was reached. Afterwards, the reaction mixtures were mixed with purple loading dye (New England Biolabs) and were run on agarose gel electrophoresis.

Example 4

PCR Cloning Using *Thermus thermophilus* Argonaute (ttAgo)

The ttAgo protein is able to use small DNA guides (13 to 25 nt) to cleave ssDNA targets at specific position (between 10 and 11nt of the guide). To show that ttAgo could be used as a designer restriction endonuclease, the xylE gene from *Pseudomonas putida* was chosen as a target gene. pUC19HZ plasmid (a variant of pUC19 plasmid) was digested by XbaI restriction enzyme and dephosphorylated. The xylE gene was PCR amplified using primers to add 16 bp corresponding to pUC19 XbaI site to each end and the PCR amplified product was digested with ttAgo using two phosphorylated DNA guides with 16 nt length to generate XbaI sticky ends. The digested PCR product was ligated into the digested backbone (the general procedure is shown in FIG. 10). The ligation product colonies were checked for correct assembly by digestion with XbaI which showed correct assembly. As a result, ttAgo can function as a designer restriction endonuclease to cleave the DNA target at a specific position and produce desired sticky ends.

ttAgo can also use multiple guides to cleave the target DNA and produce different sticky ends. As an example, pUC19HZ plasmid was cleaved by a set of different restriction enzymes, EcoRI and HindIII, XbaI and EcoRI, and XbaI and HindIII. The xylE gene was again PCR amplified to generate 16 bp sequence corresponding to each restriction site in pUC19HZ plasmid. Each PCR product was digested by ttAgo using 4 different guides in a single reaction to produce PCR products with the aforementioned sticky ends. The digested insert was ligated into pUC19HZ backbone and the correct assembly was checked by restriction digestion using the relevant set of restriction enzymes. All the checked colonies showed correct assembly.

Example 5

DNA Fingerprinting Using PfAgo AREs

To explore whether PfAgo AREs can be used for DNA fingerprinting, a linear dsDNA was selected with 10995 bp, i.e. plasmid pCRISPomyces 2 (a.k.a. pCM2) (14) linearized with Bsu36I, as a target. pCM2 has unique restriction sites for the restriction enzymes AvrII, BamHI, XbaI, and NdeI. Eight different phosphorylated DNA guides corresponding to each of the restriction sites were designed and a set of digestion experiments with PfAgo were performed (FIG. 3A). For each experiment, the same DNA target was digested with the restriction enzymes instead of PfAgo AREs to serve as positive control. In the first experiment, the linearized target was cleaved using PfAgo and AvrII guides. In the second experiment, BamHI guides were also added to the reaction mixture. The same approach was used for the third and fourth experiments by addition of XbaI and EcoRI guides to the reaction mixture until all 8 guides were present in the PfAgo reaction. PfAgo was able to generate the same pattern for the DNA target as restriction enzymes using 8 guides in the same reaction. The experiments were repeated multiple times with the same results (FIG. 3A).

One of the advantages of using PfAgo as a designer restriction enzyme is the fact that generation of a double strand break with PfAgo requires the presence of both guides targeting two different strands of DNA at positions close to each other (for example within about 1, 5, 10, 20, 50, 100, 200, 300, 400, 500 or more nucleotides of each other). If one of the guides is not present in the reaction mixture, PfAgo would not be able to cleave the dsDNA and would only create a nick on the target. This feature gives this PfAgo/ARE platform great specificity because, for example, generation of 3' sticky ends of 4 nt requires two guides targeting a 22 bp DNA sequence. To investigate whether this is actually the case, a set of DNA guides corresponding to AvrII, BamHI, and XbaI sites on pCM2 was used for PfAgo cleavage. In one experiment, one of the XbaI guides was excluded from the reaction. In another experiment, one of the XbaI guides and one of the BamHI guides were excluded from the reaction mixture. The DNA patterns for each of these experiments indeed confirmed that for DNA cleavage at one site, both guides must be present at the same time (FIG. 3B). Linearized pUC19 (with BsaI) was also used for the fingerprinting experiments. The pUC19 target was digested with PfAgo using 6 guides in the same reaction in which each set of guides were directed to generate sticky ends of varying sizes. The digestion product showed the correct pattern based on the known pUC19 sequence (FIG. 3C), demonstrating the multiplexing ability of this PfAgo/ARE platform.

Materials and Methods.

pCM2 plasmid was first digested with Bsu36I and purified using QIAQUICK® PCR purification kit (QIAGEN). For all fingerprinting experiments, around 1 μg of the linearized target was mixed in 20 μl reaction buffer with PfAgo concentrations ranging from 0.1 to 0.2 μM. The molar ratio of overall DNA guides to PfAgo was kept higher than 10:1. Reaction mixtures were incubated at 95° C. for 10 min followed by slow cooling. Upon completion of the digestion, the samples were mixed with purple loading dye (New England Biolabs) and were run on agarose gel electrophoresis. For PfAgo/AREs digestion with 8 guides at the same time, the reaction was incubated at 95° C. for 15 min instead of 10 min.

For pUC19 fingerprinting, the plasmid was first digested with BsaI and purified using QIAQUICK® PCR purification kit (QIAGEN). Around 500 ng of the digested pUC19 was mixed in 20 μl reaction buffer with PfAgo concentration of 0.2 μM and the sample was incubated at 95° C. for 20 min followed by slow cooling. The molar ratio of overall DNA guides to PfAgo was kept at 12:1.

Example 6

Genomic DNA Cloning Using PfAgo AREs

Finally, we tested whether PfAgo/AREs could be used for direct cloning of genomic DNA targets because traditional restriction enzyme-based cloning strategies are often limited by the availability of unique restriction sites in the target DNA. To this end, a random region from *Streptomyces coelicolor* A3(2) genomic DNA with ~2 kb in size was selected as a target. For this genomic DNA target, two sets of DNA guides were designed. Each set of guides was expected to produce 5' sticky ends with the size of 4 nt on each end of the target. For receiver generation, pUC19 plasmid was PCR amplified with primers containing additional DNA sequences corresponding to each end of the genomic DNA target. Both the *S. coelicolor* genomic DNA and the receiver were digested with PfAgo using the two sets of guides, and the purified DNA fragments were ligated together. The resulting plasmids were analyzed by restriction digestion and DNA sequencing and 80% of them were correct (FIG. 8).

Materials and Methods

*S. coelicolor* A3(2) genomic DNA was purified using WIZARD® genomic DNA purification kit (Promega). Around 20 μg of the genomic DNA was mixed in 400 μl reaction buffer containing PfAgo at the concentration of 0.2 μM. For the 2 kb genomic DNA target, ectoine(2)-g1, ectoine(2)-g2, ectoine(2)-g3, and ectoine(2)-g4 were used as ssDNA guides. The overall guide to PfAgo ratio was kept at 40:1. The reaction mixture was incubated at 98° C. for 10 min followed by slow cooling and the digestion product was purified by column purification using QIAQUICK® PCR purification kit (QIAGEN). pUC19 receiver was PCR amplified using the primers pUC19-ecto2-F and pUC19-ecto2-R. The PCR product was purified by agarose gel extraction using ZYMOCLEAN™ Gel DNA recovery Kit (Zymo Research) and the purified receiver was digested with the same PfAgo/AREs by incubating at 95° C. for 10 min. The digestion product was then purified by column purification and dephosphorylated using rSAP. Both purified digestion products (genomic DNA and dephosphorylated receiver) were mixed together with the ratio of 2:1 (gDNA:receiver) and were ligated together using T4 DNA ligase (Note that for gDNA the molar ratio was based on the 20 µg initial sample). The ligation mixture was incubated at room temperature for 30 min and then transformed into NEB5a competent E. coli according to manufacturer's protocol.

Example 7

DNA Assembly

A plasmid harboring the zeaxanthin pathway pAmp-EC-Zeax (FIG. 12) was chosen as a PfAgo-based ARE target. One of the advantages of using this plasmid for DNA assembly is the fact that after transformation into E. coli, the colonies containing the full plasmid will produce a yellow color product which can be used to estimate the efficiency and fidelity of correct DNA assembly. The plasmid was divided into three fragments including the backbone, (CrtE, CrtB), and (CrtI, CrtY, CrtZ) operons and the three fragments were assembled together using PfAgo-based AREs and DNA ligation.

Each of the aforementioned fragments was amplified using polymerase chain reaction (PCR). The primers used for PCR were designed such that after amplification, the fragments share 10 bp overlap with each other (FIG. 13). After PCR, each fragment was purified and the purified fragments were digested in a one-pot reaction using six different PfAgo AREs using six different DNA guides. In this example, PfAgo AREs work as DNA nickases to produce 10 nt sticky ends at the ends of each fragment. Upon PfAgo reaction, the digested fragments were purified and assembled together by DNA ligation using E. coli DNA ligase. The ligation mixture was then transformed into E. coli and ~50% of the colonies showed the yellow color which is the indicator of correct assembly. To further check the correct assembly, 5 of the yellow colonies were picked and grown in liquid culture and the purified plasmids were checked by restriction digestion (FIG. 14). All of the checked plasmids showed correct digestion pattern.

Material and Methods:

The fragments were PCR amplified using primers listed in Table 3 and Q5 Hotstart DNA Polymerase (New England Biolabs) according to the manufacturer's protocol. Before PCR amplification, the primers were phosphorylated using T4 polynucleotide kinase (New England Biolabs) according to manufacturer's protocol. After PCR amplification, each fragment was purified by agarose gel extraction using Zymoclean Gel DNA recovery Kit (Zymo Research). For PfAgo digestion, the three DNA fragments, six DNA guides (listed in Table 3), and PfAgo were all mixed in 50 µl PfAgo reaction buffer and the sample was incubated at 90° C. for 12 min and then cooled down slowly to reach 10° C. The total amount of DNA fragments was around 1 µg and the molar ratio between fragments was kept at 1:1:1. The total concentration of DNA guides was ~6 µM with the same molar ratio between each guide, and PfAgo concentration was kept at 0.25 µM. Digestion product was then purified using Qiaquick PCR purification kit (QIAGEN). For DNA ligation, ~100 ng of purified digestion product was mixed in a total of 20 µl in E. coli DNA ligase buffer (New England Biolabs) and 10 Units of E. coli ligase and the sample was incubated with the following protocol (37° C. for 30 min, 30° C. for 30 min, 65° C. for 20 min). The ligation mixture was then transformed into NEB5α competent cells (New England Biolabs) according to manufacturer's protocol and the cells were plated on LB+Ampicillin plates.

Example 8

DNA Assembly pAmp-EC-Zeax) was divided into 4 fragments including CrtE, (CrtB, CrtZ), CrtY, and CrtI genes. Each of the fragments were amplified using polymerase chain reaction (PCR). A backbone fragment was also amplified by PCR from a plasmid template (pAmp-EC). The primers used for PCR (Table 4) were designed such that after amplification, the fragments share 7 bp overlap with each other. These 7 bp overhangs were also designed to have minimal homology to each other to decrease the chance of mismatch ligation. After PCR, each fragment was purified and the purified fragments were digested in a one-pot reaction using ten different PfAgo AREs with ten different DNA guides. Like Example 7, PfAgo AREs work as DNA nickases and create 7 nt sticky ends at the ends of each fragment. Upon PfAgo reaction, the digested fragments were purified and assembled together by DNA ligation using E. coli DNA ligase. The ligation mixture was then transformed into E. coli and ~97% of the colonies showed the yellow color which is the indicator of correct assembly.

Material and Methods

The fragments were PCR amplified using primers listed in Table 4 and Q5 Hotstart DNA Polymerase (New England Biolabs) according to the manufacturer's protocol. After PCR amplification, each fragment was purified by agarose gel extraction using Zymoclean Gel DNA recovery Kit (Zymo Research). For PfAgo digestion, the five DNA fragments, ten DNA guides (listed in Table 4), and PfAgo were all mixed in 50 µl PfAgo reaction buffer (20 mM HEPES pH 7.5, 250 mM NaCl, 2 mM $MnCl_2$) and the sample was incubated at 70° C. for 15 min followed by 90° C. for 10 min and then cooled down slowly to reach 10° C. The total amount of DNA fragments was around 1 µg and the molar ratio between fragments was kept at 1:1:1:1:1. The total concentration of DNA guides was ~5 µM with the same molar ratio between each guide, and PfAgo concentration was kept at 0.1 µM. Digestion product was then purified using Qiaquick PCR purification kit (QIAGEN). For DNA ligation, ~200 ng of purified digestion product was mixed in a total of 20 µl in E. coli DNA ligase buffer (New England Biolabs) and 10 Units of E. coli ligase and the sample was incubated with the following protocol (25° C. for 30 sec, 37° C. for 30 sec, 80 cycles, 65° C. for 20 min). The ligation mixture was then transformed into NEB5α competent cells (New England Biolabs) according to manufacturer's protocol and the cells were plated on LB+Carbenicillin plates.

REFERENCES

1. M. Meselson, R. Yuan, DNA restriction enzyme from E. coli. Nature 217, 1110-1114 (1968).
2. H. O. Smith, K. W. Wilcox, A restriction enzyme from Hemophilus influenzae 0.1. Purification and general properties. J Mol Biol 51, 379-391 (1970).
3. K. Danna, D Nathans, Studies of Sv40 DNA 0.1. Specific cleavage of Simian virus 40 DNA by restriction endonuclease of Hemophilus influenzae. P Natl Acad Sci USA 68, 2913-2917 (1971).
4. D. A. Jackson, P. Berg, R. H. Symons, Biochemical method for inserting new genetic information into DNA of Simian virus 40—Circular Sv40 DNA molecules containing lambda phage genes and galactose operon of *Escherichia coli*. *P Natl Acad Sci USA* 69, 2904-& (1972).
5. R. J. Roberts, T. Vincze, J. Posfai, D. Macelis, REBASE—restriction enzymes and DNA methyltransferases. *Nucleic Acids Res* 33, D230-232 (2005).
6. R. Gupta, N. Capalash, P. Sharma, Restriction endonucleases: natural and directed evolution. *Appl Microbiol Biotechnol* 94, 583-599 (2012).
7. A. Tovkach, V. Zeevi, T. Tzfira, Expression, purification and characterization of cloning-grade zinc finger nuclease. *J Biotechnol* 151, 1-8 (2011).
8. N. Sun, H. Zhao, Transcription activator-like effector nucleases (TALENs): a highly efficient and versatile tool for genome editing. *Biotechnol Bioeng* 110, 1811-1821 (2013).
9. J. W. Wang et al., CRISPR/Cas9 nuclease cleavage combined with Gibson assembly for seamless cloning. *Biotechniques* 58, 161-170 (2015).
10. D. C. Swarts et al., Argonaute of the archaeon *Pyrococcus furiosus* is a DNA-guided nuclease that targets cognate DNA. *Nucleic Acids Res* 43, 5120-5129 (2015).
11. D. C. Swarts et al., DNA-guided DNA interference by a prokaryotic Argonaute. *Nature* 507, 258-261 (2014).
12. C. Ingram, M. Brawner, P. Youngman, J Westpheling, Xyle functions as an efficient reporter gene in *Streptomyces* Spp—use for the study of Galp1, a catabolite-controlled promoter. *J Bacteriol* 171, 6617-6624 (1989).
13. M. Jinek et al., A programmable dual-RNA-guided DNA endonuclease in adaptive bacterial immunity. *Science* 337, 816-821 (2012).
14. R. E. Cobb, Y. Wang, H. Zhao, High-efficiency multiplex genome editing of *Streptomyces* species using an engineered CRISPR/Cas system. *ACS Synth Biol* 4, 723-728 (2015).
15. Cohen, Stanley N., et al. "Construction of biologically functional bacterial plasmids in vitro." Proceedings of the National Academy of Sciences 70.11 (1973): 3240-3244.
16. Ellis, Tom, Tom Adie, and Geoff S. Baldwin. "DNA assembly for synthetic biology: from parts to pathways and beyond." Integrative Biology 3.2 (2011): 109-118.
17. Chao, Ran, Yongbo Yuan, and Huimin Zhao. "Recent advances in DNA assembly technologies." FEMS yeast research 15.1 (2015): 1-9.
18. Nour-Eldin, Hussam H., Fernando Geu-Flores, and Barbara A. Balkier. "USER cloning and USER fusion: the ideal cloning techniques for small and big laboratories." Plant secondary metabolism engineering: methods and applications (2010): 185-200.
19. Li, Mamie Z., and Stephen J. Elledge. "Harnessing homologous recombination in vitro to generate recombinant DNA via SLIC." Nature methods 4.3 (2007): 251-256.
20. Zhang, Yongwei, Uwe Werling, and Winfried Edelmann. "SLiCE: a novel bacterial cell extract-based DNA cloning method." Nucleic acids research 40.8 (2012): e55-e55.

TABLE 1

| PCR primers. | |
| --- | --- |
| xylE-F-XbaI | 5' GATCCTCTAGAGTCGAATGAACAAAGGTGTAATGCGACC 3'<br>SEQ ID NO: 1 |
| xylE-R-XbaI | 5' TCGACTCTAGAGGATCTCAGGTCAGCACGGTCATGAA 3'<br>SEQ ID NO: 2 |
| xylE-F-EcorI | 5' CCAGTGAATTCGAGCTATGAACAAAGGTGTAATGCGACC 3'<br>SEQ ID NO: 3 |
| xylE-R-EcorI | 5' AGCTCGAATTCACTGGTCAGGTCAGCACGGTCATGAA 3'<br>SEQ ID NO: 4 |
| xylE-F-HindIII | 5' CATGCAAGCTTGGCGTATGAACAAAGGTGTAATGCGACC 3'<br>SEQ ID NO: 5 |
| xylE-R-HindIII | 5' ACGCCAAGCTTGCATGTCAGGTCAGCACGGTCATGAA 3'<br>SEQ ID NO: 6 |
| cas9-F-XbaI | 5' GATCCTCTAGAGTCGAATGGACAAGAAGTACAGCATCGG 3'<br>SEQ ID NO: 7 |
| cas9-R-XbaI | 5' TCGACTCTAGAGGATCTCAGTCGCCGCCGAGC 3'<br>SEQ ID NO: 8 |
| cas9-F-EcorI | 5' CCAGTGAATTCGAGCTATGGACAAGAAGTACAGCATCGG 3'<br>SEQ ID NO: 9 |
| cas9-R-EcorI | 5' AGCTCGAATTCACTGGTCAGTCGCCGCCGAGC 3'<br>SEQ ID NO: 10 |
| cas9-F-HindIII | 5' CATGCAAGCTTGGCGTATGGACAAGAAGTACAGCATCGG 3'<br>SEQ ID NO: 11 |
| cas9-R-HindIII | 5' ACGCCAAGCTTGCATGTCAGTCGCCGCCGAGC 3'<br>SEQ ID NO: 12 |
| xylE-F-BamHI | 5' CCCGGGGATCCTCTAGATGAACAAAGGTGTAATGCGACC 3'<br>SEQ ID NO: 13 |
| xylE-R-BamHI | 5' CTAGAGGATCCCCGGGTCAGGTCAGCACGGTCATGAA 3'<br>SEQ ID NO: 14 |

TABLE 1-continued

PCR primers.

| | | |
|---|---|---|
| xylE-F-NdeI | 5' GTGCACCATATGCGGTGTATGAACAAAGGTGTAATGCGACC 3' | SEQ ID NO: 15 |
| xylE-R-NdeI | 5' ACACCGCATATGGTGCACTCAGGTCAGCACGGTCATGAA 3' | SEQ ID NO: 16 |
| xylE-F-PfoI | 5' GCAGCTCCCGGAGACGGATGAACAAAGGTGTAATGCGACC 3' | SEQ ID NO: 17 |
| xylE-R-PfoI | 5' CCGTCTCCGGGAGCTGCTCAGGTCAGCACGGTCATGAA 3' | SEQ ID NO: 18 |
| cas9-F-BamHI | 5' CCCGGGGATCCTCTAGATGGACAAGAAGTACAGCATCGG 3' | SEQ ID NO: 19 |
| cas9-R-BamHI | 5' CTAGAGGATCCCCGGGTCAGTCGCCGCCGAGC 3' | SEQ ID NO: 20 |
| cas9-F-NdeI | 5' GTGCACCATATGCGGTGTATGGACAAGAAGTACAGCATCGG 3' | SEQ ID NO: 21 |
| cas9-R-NdeI | 5' ACACCGCATATGGTGCACTCAGTCGCCGCCGAGC 3' | SEQ ID NO: 22 |
| cas9-F-PfoI | 5' GCAGCTCCCGGAGACGGATGGACAAGAAGTACAGCATCGG 3' | SEQ ID NO: 23 |
| cas9-R-PfoI | 5' CCGTCTCCGGGAGCTGCTCAGTCGCCGCCGAGC 3' | SEQ ID NO: 24 |
| xylE-F-random-clon | 5' GCTTGTCTGTAAGCGGATGAACAAAGGTGTAATGCGACC 3' | SEQ ID NO: 25 |
| xylE-R-random-clon | 5' ATTCATTAATGCAGCTTCAGGTCAGCACGGTCATGAA 3' | SEQ ID NO: 26 |
| cas9-F-random-clon | 5' GCTTGTCTGTAAGC'GGATGGACAAGAAGTACAGCATCGG 3' | SEQ ID NO: 27 |
| cas9-R-random-clon | 5' ATTCATTAATGCAGCTTCAGTCGCCGCCGAGC 3' | SEQ ID NO: 28 |
| pUC19-Ecto2F | 5' CGCATGCGGTGGTCGAAAGCTTTGCGTTGCGCTCACTGC 3' | SEQ ID NO: 29 |
| pUC19-Ecto2-R | 5' GGACGGACTCATAAGTAAGCTTCCAACACCCGCTGACGCG 3' | SEQ ID NO: 30 |

TABLE 2

DNA guides used in this study.

| | | |
|---|---|---|
| pUC19-EcorI-g1 | 5' p-TGCTCGAATTCACTGG 3' | SEQ ID NO: 31 |
| pUC19-EcorI-g2 | 5' p-TCAGTGAATTCGAGCT 3' | SEQ ID NO: 32 |
| pUC19-HindIII-g1 | 5' p-TCGCCAAGCTTGCATG 3' | SEQ ID NO: 33 |
| pUC19-HindIII-g2 | 5' p-TATGCAAGCTTGGCGT 3' | SEQ ID NO: 34 |
| pUC19-XbaI-g1 | 5' p-TCGACTCTAGAGGATC 3' | SEQ ID NO: 35 |
| pUC19-XbaI-g2 | 5' p-TATCCTCTAGAGTCGA 3' | SEQ ID NO: 36 |
| pUC19-g7 | 5' p-CGATCTTCACCTAGAT 3' | SEQ ID NO: 37 |
| pUC19-BamHI-g1 | 5' p-TTAGAGGATCCCCGGG 3' | SEQ ID NO: 38 |
| pUC19-BamHI-g2 | 5' p-TCCGGGGATCCTCTAG 3' | SEQ ID NO: 39 |
| pUC19-NdeI-g1 | 5' p-TCACCGCATATGGTGC 3' | SEQ ID NO: 40 |
| pUC19-NdeI-g2 | 5' p-TTGCACCATATGCGGT 3' | SEQ ID NO: 41 |
| pUC19-PfoI-g1 | 5' p-TGTCTCCGGGAGCTGC 3' | SEQ ID NO: 42 |
| pUC19-PfoI-g2 | 5' p-TAGCTCCCGGAGACGG 3' | SEQ ID NO: 43 |
| pUC19-random-g1 | 5' p-TGCTGCATTAATGAAT 3' | SEQ ID NO: 44 |
| pUC19-random-g2 | 5' p-TTTCATTAATGCAGCT 3' | SEQ ID NO: 45 |

TABLE 2-continued

DNA guides used in this study.

| | |
|---|---|
| pUC19-random-g3 | 5' p-TCTTGTCTGTAAGCGG 3' SEQ ID NO: 46 |
| pUC19-random-g4 | 5' p-TCGCTTACAGACAAGC 3' SEQ ID NO: 47 |
| pUC19-fp-g1 | 5' p-TTCGGTCGTTCGGCTG 3' SEQ ID NO: 48 |
| pUC19-fp-g2 | 5' p-TAGCCGAACGACCGAG 3' SEQ ID NO: 49 |
| pUC19-fp-g3 | 5' p-TTGGTTATGGCAGCAC 3' SEQ ID NO: 50 |
| pUC19-fp-g4 | 5' p-TGCAGTGCTGCCATAA 3' SEQ ID NO: 51 |
| pUC19-fp-g5 | 5' p-TTTCTTAGACGTCAGG 3' SEQ ID NO: 52 |
| pUC19-fp-g6 | 5' p-TGTGCCACCTGACGTC 3' SEQ ID NO: 53 |
| pCM2-BamHI-g1 | 5' p-TTACGGGATCCGGAAG 3' SEQ ID NO: 54 |
| pCM2-BamHI-g2 | 5' p-TTTCCGGATCCCGTAC 3' SEQ ID NO: 55 |
| pCM2-EcoRI-g1 | 5' p-TATCTGAATTCTCAGT 3' SEQ ID NO: 56 |
| pCM2-EcoRI-g2 | 5' p-TCTGAGAATTCAGATC 3' SEQ ID NO: 57 |
| pCM2-XbaI-g1 | 5' p-CGGCCTCTAGATAAAA 3' SEQ ID NO: 58 |
| pCM2-XbaI-g2 | 5' p-CTTTATCTAGAGGCCA 3' SEQ ID NO: 59 |
| pCM2-AvrII-g1 | 5' p-TAGCGCCTAGGTTTCT 3' SEQ ID NO: 60 |
| pCM2-AvrII-g2 | 5' p-TGAAACCTAGGCGCTG 3' SEQ ID NO: 61 |
| Ectoine(2)-g1 | 5' p-TGACGGACTCATAAGT 3' SEQ ID NO: 62 |
| Ectoine(2)-g2 | 5' p-TCTTATGAGTCCGTCC 3' SEQ ID NO: 63 |
| Ectoine(2)-g3 | 5' p-CCGACCACCGCATGCG 3' SEQ ID NO: 64 |
| Ectoine(2)-g4 | 5' p-TGCATGCGGTGGTCGA 3' SEQ ID NO: 65 |

TABLE 3

PCR primers and DNA guides

PCR primers

| | |
|---|---|
| Fragment1-F | 5' AACGGTGTGCATCAGCTCACTCAAAGGCGG 3' SEQ ID NO: 83 |
| Fragment1-R | 5' AAGACGAGGGAAAGGGCCTCGTGATACGC 3' SEQ ID NO: 84 |
| Fragment2-F | 5' CCCTCGTCTTGACAGGCATGCATAAGG 3' SEQ ID NO: 85 |

TABLE 3-continued

PCR primers and DNA guides

| | |
|---|---|
| Fragment2-R | 5'AAGTAAACCGCGTTAAAAAATATCCCCGGTAGCTGAC 3' SEQ ID NO: 86 |
| Fragment3-F | 5' CGGTTTACTTCCCGGATGCGGG 3' SEQ ID NO: 87 |
| Fragment3-R | 5' GCACACCGTTGACGGCTAGCTCA 3' SEQ ID NO: 88 |

DNA guides

| | |
|---|---|
| 3f-g1 | 5' p-TACGGTGTGCATCAGC 3' SEQ ID NO: 89 |
| 3f-g2 | 5' p-TAGACGAGGGAAAGGG 3' SEQ ID NO: 90 |
| 3f-g3 | 5' p-TAGTAAACCGCGTTAA 3' SEQ ID NO: 91 |
| 3f-g4 | 5' p-TCCTCGTCTTGACAGG 3' SEQ ID NO: 92 |
| 3f-g5 | 5' p-TGGTTTACTTCCCGGA 3' SEQ ID NO: 93 |
| 3f-g6 | 5' p-TCACACCGTTGACGGC 3' SEQ ID NO: 94 |

TABLE 4

PCR primers and DNA guides

PCR primers

| | |
|---|---|
| pAmp-F | acgaaggGTGCATCAGCTCACTCAAAGGC SEQ ID NO: 95 |
| pAMP-R | GtcaacgAGGGAAAGGGCCTCGTGAT SEQ ID NO: 96 |
| crtE-F | CgttgacCCCTCGTCTTGACAGGCAT SEQ ID NO: 97 |
| crtE-R | TgacgtcTTAACTGACGGCAGCGAGTT SEQ ID NO: 98 |
| crtBZ-F | GacgtcaTCCAGAATTAATTACTATAGTCACTAGAG SEQ ID NO: 99 |
| crtBZ-R | CaggctaATCGTACTCAAAATCTTTACTTAGGAG SEQ ID NO: 100 |
| crtY-F | TagcctgTTAACGATGAGTCGTCATAATGGCTTGC SEQ ID NO: 101 |
| crtY-R | CgactcaAGATACGACTAAGGAAGTTTCAATGCAACC SEQ ID NO: 102 |
| crtZ-F | TgagtcgTCATATCAGATCCTCCAGCATCAAACC SEQ ID NO: 103 |
| crtZ-R | CcttcgtGCACACCGTTGACGGCTAG SEQ ID NO: 104 |

DNA guides

| | |
|---|---|
| 5f-g1 | 5' p-GCTGATGCACccttcg SEQ ID NO: 105 |
| 5f-g2 | 5' p-CCCTTTCCCTcgttga SEQ ID NO: 106 |
| 5f-g3 | 5' p-AAGACGAGGGgtcaac SEQ ID NO: 107 |
| 5f-g4 | 5' p-CGTCAGTTAAgacgtc SEQ ID NO: 108 |

TABLE 4-continued

PCR primers and DNA guides

| | | |
|---|---|---|
| 5f-g5 | 5' p-TAATTCTGGAtgacgt | SEQ ID NO: 109 |
| 5f-g6 | 5' p-TGAGTACGATtagcct | SEQ ID NO: 110 |
| 5f-g7 | 5' p-TCATCGTTAAcaggct | SEQ ID NO: 111 |

TABLE 4-continued

PCR primers and DNA guides

| | | |
|---|---|---|
| 5f-g8 | 5' p-AGTCGTATCTtgagtc | SEQ ID NO: 112 |
| 5f-g9 | 5' p-TCTGATATGAcgactc | SEQ ID NO: 113 |
| 5f-g10 | 5' p-AACGGTGTGCacgaag | SEQ ID NO: 114 |

We claim:

1. A composition comprising:
   (a) an isolated *Pyrococcus furiosus* argonaute ("PfAgo") protein,
   (b) one or more double-stranded linear target DNA molecules,
   (c) one or more single-stranded DNA guides that have complementarity to the one or more double-stranded linear target DNA molecules that, when combined with the double-stranded linear target DNA molecules and the isolated PfAgo protein, generate one or more double-stranded linear target DNA molecules having altered 5 or 3' overhanging ends or blunt ends, and
   (d) a plasmid having complementary ends to the one or more double-stranded linear target DNA molecules having altered 5' or 3° overhanging ends or blunt ends generated by the combination of the one or more single-stranded DNA guides, the double-stranded linear target DNA molecules, and the isolated PfAgo protein,
   wherein the PfAgo protein and one or more single-stranded DNA guides do not naturally occur together.

2. The composition of claim 1, wherein the one or more single-stranded DNA guides are about 9 to about 60 nucleotides in length.

3. The composition of claim 1, wherein the one or more double-stranded linear target DNA molecules are methylated.

4. The composition of claim 1, wherein the one or more double-stranded linear target DNA molecules are eukaryotic, prokaryotic, or synthetic DNA molecules.

5. The composition of claim 1, wherein the one or more DNA guides are synthetic DNA molecules.

6. The composition of claim 1, wherein the one or more DNA guides are 5'-phosphorylated.

7. The composition of claim 1, comprising one or more single-stranded DNA guides that have complementarity to one or more double-stranded linear target DNA molecules that, when combined with the double-stranded linear target DNA molecules and the isolated PfAgo protein, generate one or more double-stranded linear target DNA molecules having different lengths or sequences of altered 5' or 3' overhanging ends or blunt ends.

8. The composition of claim 1, wherein the overhanging ends are 1, 2, 3, 4, 5, 6, 7, 8, 9, 10, 11, 12 or more nucleotides in length.

9. The composition of claim 1, wherein the overhanging ends are 2, 3, 4, 5, 6, 7, or 8 nucleotides in length.

10. The composition of claim 1, wherein the one or more single-stranded DNA guides are 10, 11, 12, 13, 14, 15, 16, 17, or 18 nucleotides in length.

* * * * *

SEQUENCE LISTING

<160> NUMBER OF SEQ ID NOS: 122

<210> SEQ ID NO 1
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 1
gatcctctag agtcgaatga acaaaggtgt aatgcgacc                39

<210> SEQ ID NO 2
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 2
tcgactctag aggatctcag gtcagcacgg tcatgaa                  37

<210> SEQ ID NO 3
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 3
ccagtgaatt cgagctatga acaaaggtgt aatgcgacc                39

<210> SEQ ID NO 4
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 4
agctcgaatt cactggtcag gtcagcacgg tcatgaa                  37

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
catgcaagct tggcgtatga acaaaggtgt aatgcgacc                39

<210> SEQ ID NO 6
<211> LENGTH: 37

```
<212> TYPE: DNA
<213> ORGANISM: Artificial Sequence
<220> FEATURE:
<223> OTHER INFORMATION: Synthetic oligonucleotide

<400> SEQUENCE: 6
acgccaagct tgcatgtcag gtcagcacgg tcatgaa                              37

<210> SEQ ID NO 7
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 7
gatcctctag agtcgaatgg acaagaagta cagcatcgg                            39

<210> SEQ ID NO 8
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 8
tcgactctag aggatctcag tcgccgccga gc                                   32

<210> SEQ ID NO 9
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 9
ccagtgaatt cgagctatgg acaagaagta cagcatcgg                            39

<210> SEQ ID NO 10
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 10
agctcgaatt cactggtcag tcgccgccga gc                                   32

<210> SEQ ID NO 11
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 11
catgcaagct tggcgtatgg acaagaagta cagcatcgg                            39

<210> SEQ ID NO 12
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 12
```

```
acgccaagct tgcatgtcag tcgccgccga gc                              32
```

<210> SEQ ID NO 13
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 13

```
cccggggatc ctctagatga acaaaggtgt aatgcgacc                       39
```

<210> SEQ ID NO 14
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 14

```
ctagaggatc cccgggtcag gtcagcacgg tcatgaa                         37
```

<210> SEQ ID NO 15
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 15

```
gtgcaccata tgcggtgtat gaacaaaggt gtaatgcgac c                    41
```

<210> SEQ ID NO 16
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 16

```
acaccgcata tggtgcactc aggtcagcac ggtcatgaa                       39
```

<210> SEQ ID NO 17
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 17

```
gcagctcccg gagacggatg aacaaaggtg taatgcgacc                      40
```

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 18

```
ccgtctccgg gagctgctca ggtcagcacg gtcatgaa                        38
```

<210> SEQ ID NO 19
<211> LENGTH: 39
<212> TYPE: DNA
<213> ORGANISM: Artificial Sequence

```
<220> FEATURE:
<223> OTHER INFORMATION: Synthetic oligonucleotide

<400> SEQUENCE: 19
cccggggatc tctagatgg acaagaagta cagcatcgg                    39

<210> SEQ ID NO 20
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 20
ctagaggatc cccgggtcag tcgccgccga gc                          32

<210> SEQ ID NO 21
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 21
gtgcaccata tgcggtgtat ggacaagaag tacagcatcg g                41

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 22
acaccgcata tggtgcactc agtcgccgcc gagc                        34

<210> SEQ ID NO 23
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 23
gcagctcccg gagacggatg gacaagaagt acagcatcgg                  40

<210> SEQ ID NO 24
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 24
ccgtctccgg gagctgctca gtcgccgccg agc                         33

<210> SEQ ID NO 25
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 25
gcttgtctgt aagcggatga acaaaggtgt aatgcgacc                   39
```

-continued

<210> SEQ ID NO 26
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 26
attcattaat gcagcttcag gtcagcacgg tcatgaa                37

<210> SEQ ID NO 27
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 27
gcttgtctgt aagcggatgg acaagaagta cagcatcgg              39

<210> SEQ ID NO 28
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 28
attcattaat gcagcttcag tcgccgccga gc                     32

<210> SEQ ID NO 29
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 29
cgcatgcggt ggtcgaaagc tttgcgttgc gctcactgc              39

<210> SEQ ID NO 30
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 30
ggacggactc ataagtaagc ttccaacacc cgctgacgcg             40

<210> SEQ ID NO 31
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 31
tgctcgaatt cactgg                                       16

<210> SEQ ID NO 32
<211> LENGTH: 16

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc
<222> LOCATION: (1)..(1)
<223> OTHER INFORMATION: 5' phosphate

<400> SEQUENCE: 32
tcagtgaatt cgagct                                                 16

<210> SEQ ID NO 33
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 33
tcgccaagct tgcatg                                                 16

<210> SEQ ID NO 34
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 34
tatgcaagct tggcgt                                                 16

<210> SEQ ID NO 35
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 35
tcgactctag aggatc                                                 16

<210> SEQ ID NO 36
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 36
tatcctctag agtcga                                                 16

<210> SEQ ID NO 37
```

```
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 37
cgatcttcac ctagat                                               16

<210> SEQ ID NO 38
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 38
ttagaggatc cccggg                                               16

<210> SEQ ID NO 39
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 39
tccggggatc ctctag                                               16

<210> SEQ ID NO 40
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 40
tcaccgcata tggtgc                                               16

<210> SEQ ID NO 41
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 41
ttgcaccata tgcggt                                               16
```

```
<210> SEQ ID NO 42
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 42
tgtctccggg agctgc                                                   16

<210> SEQ ID NO 43
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 43
tagctcccgg agacgg                                                   16

<210> SEQ ID NO 44
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 44
tgctgcatta atgaat                                                   16

<210> SEQ ID NO 45
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 45
tttcattaat gcagct                                                   16

<210> SEQ ID NO 46
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 46
tcttgtctgt aagcgg                                                   16
```

```
<210> SEQ ID NO 47
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 47
tcgcttacag acaagc                                              16

<210> SEQ ID NO 48
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 48
ttcggtcgtt cggctg                                              16

<210> SEQ ID NO 49
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 49
tagccgaacg accgag                                              16

<210> SEQ ID NO 50
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 50
ttggttatgg cagcac                                              16

<210> SEQ ID NO 51
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 51
tgcagtgctg ccataa                                              16
```

```
<210> SEQ ID NO 52
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 52
tttcttagac gtcagg                                                        16

<210> SEQ ID NO 53
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 53
tgtgccacct gacgtc                                                        16

<210> SEQ ID NO 54
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 54
ttacgggatc cggaag                                                        16

<210> SEQ ID NO 55
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 55
tttccggatc ccgtac                                                        16

<210> SEQ ID NO 56
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 56
```

```
tatctgaatt ctcagt                                                    16
```

<210> SEQ ID NO 57
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 57

```
tctgagaatt cagatc                                                    16
```

<210> SEQ ID NO 58
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 58

```
cggcctctag ataaaa                                                    16
```

<210> SEQ ID NO 59
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 59

```
ctttatctag aggcca                                                    16
```

<210> SEQ ID NO 60
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 60

```
tagcgcctag gtttct                                                    16
```

<210> SEQ ID NO 61
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 61
tgaaacctag gcgctg                                                    16

<210> SEQ ID NO 62
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 62
tgacggactc ataagt                                                    16

<210> SEQ ID NO 63
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 63
tcttatgagt ccgtcc                                                    16

<210> SEQ ID NO 64
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 64
ccgaccaccg catgcg                                                    16

<210> SEQ ID NO 65
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 65
tgcatgcggt ggtcga                                                    16

<210> SEQ ID NO 66
<211> LENGTH: 770
<212> TYPE: PRT
<213> ORGANISM: Artificial Sequence
<220> FEATURE:
<223> OTHER INFORMATION: Synthetic amino acid sequence

<400> SEQUENCE: 66

Met Lys Ala Lys Val Val Ile Asn Leu Val Lys Ile Asn Lys Lys Ile
1               5                   10                  15

```
Ile Pro Asp Lys Ile Tyr Val Tyr Arg Leu Phe Asn Asp Pro Glu Glu
            20                  25                  30

Glu Leu Gln Lys Glu Gly Tyr Ser Ile Tyr Arg Leu Ala Tyr Glu Asn
            35                  40                  45

Val Gly Ile Val Ile Asp Pro Glu Asn Leu Ile Ile Ala Thr Thr Lys
 50                      55                  60

Glu Leu Glu Tyr Glu Gly Glu Phe Ile Pro Glu Gly Glu Ile Ser Phe
 65                  70                  75                  80

Ser Glu Leu Arg Asn Asp Tyr Gln Ser Lys Leu Val Leu Arg Leu Leu
                85                  90                  95

Lys Glu Asn Gly Ile Gly Glu Tyr Glu Leu Ser Lys Leu Leu Arg Lys
            100                 105                 110

Phe Arg Lys Pro Lys Thr Phe Gly Asp Tyr Lys Val Ile Pro Ser Val
            115                 120                 125

Glu Met Ser Val Ile Lys His Asp Glu Asp Phe Tyr Leu Val Ile His
130                 135                 140

Ile Ile His Gln Ile Gln Ser Met Lys Thr Leu Trp Glu Leu Val Asn
145                 150                 155                 160

Lys Asp Pro Lys Glu Leu Glu Glu Phe Leu Met Thr His Lys Glu Asn
            165                 170                 175

Leu Met Leu Lys Asp Ile Ala Ser Pro Leu Lys Thr Val Tyr Lys Pro
            180                 185                 190

Cys Phe Glu Glu Tyr Thr Lys Lys Pro Lys Leu Asp His Asn Gln Glu
            195                 200                 205

Ile Val Lys Tyr Trp Tyr Asn Tyr His Ile Glu Arg Tyr Trp Asn Thr
            210                 215                 220

Pro Glu Ala Lys Leu Glu Phe Tyr Arg Lys Phe Gly Gln Val Asp Leu
225                 230                 235                 240

Lys Gln Pro Ala Ile Leu Ala Lys Phe Ala Ser Lys Ile Lys Lys Asn
                245                 250                 255

Lys Asn Tyr Lys Ile Tyr Leu Leu Pro Gln Leu Val Val Pro Thr Tyr
            260                 265                 270

Asn Ala Glu Gln Leu Glu Ser Asp Val Ala Lys Glu Ile Leu Glu Tyr
            275                 280                 285

Thr Lys Leu Met Pro Glu Glu Arg Lys Glu Leu Leu Glu Asn Ile Leu
            290                 295                 300

Ala Glu Val Asp Ser Asp Ile Ile Asp Lys Ser Leu Ser Glu Ile Glu
305                 310                 315                 320

Val Glu Lys Ile Ala Gln Glu Leu Glu Asn Lys Ile Arg Val Arg Asp
                325                 330                 335

Asp Lys Gly Asn Ser Val Pro Ile Ser Gln Leu Asn Val Gln Lys Ser
            340                 345                 350

Gln Leu Leu Leu Trp Thr Asn Tyr Ser Arg Lys Tyr Pro Val Ile Leu
            355                 360                 365

Pro Tyr Glu Val Pro Glu Lys Phe Arg Lys Ile Arg Glu Ile Pro Met
            370                 375                 380

Phe Ile Ile Leu Asp Ser Gly Leu Leu Ala Asp Ile Gln Asn Phe Ala
385                 390                 395                 400

Thr Asn Glu Phe Arg Glu Leu Val Lys Ser Met Tyr Tyr Ser Leu Ala
                405                 410                 415

Lys Lys Tyr Asn Ser Leu Ala Lys Ala Arg Ser Thr Asn Glu Ile
            420                 425                 430
```

```
Gly Leu Pro Phe Leu Asp Phe Arg Gly Lys Glu Lys Val Ile Thr Glu
            435                 440                 445

Asp Leu Asn Ser Asp Lys Gly Ile Ile Glu Val Val Glu Gln Val Ser
    450                 455                 460

Ser Phe Met Lys Gly Lys Glu Leu Gly Leu Ala Phe Ile Ala Ala Arg
465                 470                 475                 480

Asn Lys Leu Ser Ser Glu Lys Phe Glu Ile Lys Arg Arg Leu Phe
                485                 490                 495

Asn Leu Asn Val Ile Ser Gln Val Val Asn Glu Asp Thr Leu Lys Asn
            500                 505                 510

Lys Arg Asp Lys Tyr Asp Arg Asn Arg Leu Asp Leu Phe Val Arg His
        515                 520                 525

Asn Leu Leu Phe Gln Val Leu Ser Lys Leu Gly Val Lys Tyr Tyr Val
    530                 535                 540

Leu Asp Tyr Arg Phe Asn Tyr Asp Tyr Ile Ile Gly Ile Asp Val Ala
545                 550                 555                 560

Pro Met Lys Arg Ser Glu Gly Tyr Ile Gly Gly Ser Ala Val Met Phe
                565                 570                 575

Asp Ser Gln Gly Tyr Ile Arg Lys Ile Val Pro Ile Lys Ile Gly Glu
            580                 585                 590

Gln Arg Gly Glu Ser Val Asp Met Asn Glu Phe Phe Lys Glu Met Val
        595                 600                 605

Asp Lys Phe Lys Glu Phe Asn Ile Lys Leu Asp Asn Lys Lys Ile Leu
    610                 615                 620

Leu Leu Arg Asp Gly Arg Ile Thr Asn Asn Glu Glu Glu Gly Leu Lys
625                 630                 635                 640

Tyr Ile Ser Glu Met Phe Asp Ile Glu Val Val Thr Met Asp Val Ile
                645                 650                 655

Lys Asn His Pro Val Arg Ala Phe Ala Asn Met Lys Met Tyr Phe Asn
            660                 665                 670

Leu Gly Gly Ala Ile Tyr Leu Ile Pro His Lys Leu Lys Gln Ala Lys
        675                 680                 685

Gly Thr Pro Ile Pro Ile Lys Leu Ala Lys Arg Ile Ile Lys Asn
    690                 695                 700

Gly Lys Val Glu Lys Gln Ser Ile Thr Arg Gln Asp Val Leu Asp Ile
705                 710                 715                 720

Phe Ile Leu Thr Arg Leu Asn Tyr Gly Ser Ile Ser Ala Asp Met Arg
                725                 730                 735

Leu Pro Ala Pro Val His Tyr Ala His Lys Phe Ala Asn Ala Ile Arg
            740                 745                 750

Asn Glu Trp Lys Ile Lys Glu Glu Phe Leu Ala Glu Gly Phe Leu Tyr
        755                 760                 765

Phe Val
770

<210> SEQ ID NO 67
<211> LENGTH: 2313
<212> TYPE: DNA
<213> ORGANISM: Artificial Sequence
<220> FEATURE:
<223> OTHER INFORMATION: Synthetic oligonucleotide

<400> SEQUENCE: 67
atgaaggcga aggttgtgat caacctggtt aagatcaaca agaaaatcat cccggataag      60
atttacgttt accgtctgtt caacgacccg gaggaagagc tgcagaaaga gggttatagc     120
```

```
atctaccgtc tggcgtatga aaacgtgggc atcgttattg atccggagaa cctgatcatt      180
gcgaccacca aggagctgga atacgagggc gagttcatcc cggagggcga aattagcttt      240
agcgaactgc gtaacgacta tcaaagcaag ctggtgctgc gtctgctgaa agagaacggt      300
atcggcgagt acgaactgag caaactgctg cgtaagttcc gtaagccgaa aacctttggt      360
gactataaag tgatcccgag cgttgaaatg agcgtgatta agcacgacga ggatttctac      420
ctggttatcc acatcattca ccagattcaa agcatgaaaa ccctgtggga actggtgaac      480
aaggacccga agagctgga agagttcctg atgacccaca aggaaaacct gatgctgaaa      540
gacatcgcga gcccgctgaa aaccgtttat aagccgtgct ttgaagagta caccaagaaa      600
ccgaaactgg atcacaacca ggaaattgtg aagtactggt ataactacca tcgagcgt       660 tattggaaca ccccggaagc gaagctggag ttctaccgta aatttggcca ggttgacctg      720
aagcaaccgg cgatcctggc gaaatttgcg agcaagatta gaaaaacaa gaactacaaa      780 atctacctgc tgccgcagct ggttgtgccg acctataacg cggaacaact ggagagcgat      840
gttgcgaagg aaattctgga gtacaccaaa ctgatgccgg aagagcgtaa ggaactgctg      900
gagaacatcc tggcggaagt ggacagcgac atcattgaca aaagcctgag cgagatcgaa      960
gttgagaaga ttgcgcagga actggagaac aaaattcgtg tgcgtgacga taagggtaac     1020
agcgttccga tcagccaact gaacgtgcag aaaagccaac tgctgctgtg gaccaactat     1080
agccgtaagt acccggttat cctgccgtac gaagtgccgg agaagttccg taaaatccgt     1140
gaaattccga tgtttatcat tctggacagc ggcctgctgg cggacatcca gaacttcgcg     1200
accaacgaat tcgtgagcct ggtgaaaagc atgtactata gcctggcgaa gaaatacaac     1260
agcctggcga gaaagcgcg tagcaccaac gagattggtc tgccgttcct ggattttcgt     1320
ggcaaggaaa aagttatcac cgaggacctg aacagcgata agggtatcat tgaagtggtt     1380
gagcaagtga gcagcttcat gaagggtaaa gaactgggcc tggcgtttat cgcggcgcgt     1440
aacaaactga gcagcgagaa gttcgaagag attaaacgtc gtctgtttaa cctgaacgtt     1500
atcagccagg tggttaacga agatacccctg aagaacaaac gtgacaaata tgatcgtaac     1560
cgtctggacc tgttcgttcg tcacaacctg ctgtttcaag tgctgagcaa actgggtgtt     1620
aagtactatg tgctggacta ccgtttcaac tacgattaca tcatcggtat cgacgtggcg     1680
ccgatgaagc gtagcgaagg ctatatcggt ggcagcgcgg ttatgtttga cagccagggc     1740
tacatccgta agattgtgcc gatcaaaatt ggtgaacaac gtggcgagag cgttgatatg     1800
aacgagttct tcaaagagat ggtggacaag ttcaaagagt ttaacatcaa gctggataac     1860
aagaaaattc tgctgctgcg tgacggtcgt attaccaaca acgaagagga aggcctgaaa     1920
tacatcagcg aaatgttcga tattgaggtg gttacgatgg acgttatcaa aaaccacccg     1980
gtgcgtgcgt tcgcgaacat gaagatgtat tttaacctgg tggcgcgcat ctacctgatt     2040
ccgcacaagc tgaaacaggc gaaaggcacc ccgatcccga ttaagctggc gaagaaacgt     2100
atcattaaga acggcaaagt tgagaagcag agcattaccc gtcaagacgt gctggacatc     2160
ttcattctga cccgtctgaa ctatggtagc atcagcgcgg acatgcgtct gccggcgccg     2220
gttcactatg cgcacaagtt tgcgaacgcg atccgtaatg aatggaagat caaagaggag     2280
tttctggcgg agggttttct gtatttcgtg taa                                  2313

<210> SEQ ID NO 68
<211> LENGTH: 12
<212> TYPE: DNA
```

-continued

```
<213> ORGANISM: Artificial Sequence
<220> FEATURE:
<223> OTHER INFORMATION: Synthetic oligonucleotide

<400> SEQUENCE: 68
agatagcatt ta                                                          12

<210> SEQ ID NO 69
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 69 gctaat                                                                  6

<210> SEQ ID NO 70
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 70 ctatct                                                                  6

<210> SEQ ID NO 71
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 71
attagctaaa tg                                                          12

<210> SEQ ID NO 72
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 72
agatagcatt tagctaat                                                    18

<210> SEQ ID NO 73

<400> SEQUENCE: 73

000

<210> SEQ ID NO 74

<400> SEQUENCE: 74

000

<210> SEQ ID NO 75
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 75
```

```
attagctaaa tgctatct                                                   18

<210> SEQ ID NO 76
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 76
gagcatatcg gcc                                                        13

<210> SEQ ID NO 77
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 77
ggccgatatg ctc                                                        13

<210> SEQ ID NO 78
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 78
aatcaaactg attaggcata atcggg                                          26

<210> SEQ ID NO 79
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 79
tgcctaatca gtttga                                                     16

<210> SEQ ID NO 80
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 80
aatcaaactg attaggcata atcggg                                          26

<210> SEQ ID NO 81
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 81 aaggct                                                                6

<210> SEQ ID NO 82
<211> LENGTH: 6
<212> TYPE: DNA
```

<210> SEQ ID NO 82
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 82 agcctt                                                                    6

<210> SEQ ID NO 83
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 83
aacggtgtgc atcagctcac tcaaaggcgg                                         30

<210> SEQ ID NO 84
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 84
aagacgaggg aaagggcctc gtgatacgc                                          29

<210> SEQ ID NO 85
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 85
ccctcgtctt gacaggcatg cataagg                                            27

<210> SEQ ID NO 86
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 86
aagtaaaccg cgttaaaaaa tatccccggt agctgac                                 37

<210> SEQ ID NO 87
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 87
cggtttactt cccggatgcg gg                                                 22

<210> SEQ ID NO 88
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 88
gcacaccgtt gacggctagc tca                                                23

```
<210> SEQ ID NO 89
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 89
tacggtgtgc atcagc                                                       16

<210> SEQ ID NO 90
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 90
tagacgaggg aaaggg                                                       16

<210> SEQ ID NO 91
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 91
tagtaaaccg cgttaa                                                       16

<210> SEQ ID NO 92
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 92
tcctcgtctt gacagg                                                       16

<210> SEQ ID NO 93
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 93
```

```
tggtttactt cccgga                                              16
```

<210> SEQ ID NO 94
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 94

```
tcacaccgtt gacggc                                              16
```

<210> SEQ ID NO 95
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 95

```
acgaagggtg catcagctca ctcaaaggc                                29
```

<210> SEQ ID NO 96
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 96

```
gtcaacgagg gaaagggcct cgtgat                                   26
```

<210> SEQ ID NO 97
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 97

```
cgttgacccc tcgtcttgac aggcat                                   26
```

<210> SEQ ID NO 98
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 98

```
tgacgtctta actgacggca gcgagtt                                  27
```

<210> SEQ ID NO 99
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 99

```
gacgtcatcc agaattaatt actatagtca ctagag                        36
```

<210> SEQ ID NO 100
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 100
caggctaatc gtactcaaaa tctttactta ggag          34

<210> SEQ ID NO 101
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 101
tagcctgtta acgatgagtc gtcataatgg cttgc          35

<210> SEQ ID NO 102
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 102
cgactcaaga tacgactaag gaagtttcaa tgcaacc          37

<210> SEQ ID NO 103
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 103
tgagtcgtca tatcagatcc tccagcatca aacc          34

<210> SEQ ID NO 104
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 104
ccttcgtgca caccgttgac ggctag          26

<210> SEQ ID NO 105
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 105
gctgatgcac ccttcg          16

<210> SEQ ID NO 106
<211> LENGTH: 16
<212> TYPE: DNA

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 106
ccctttccct cgttga                                                      16

<210> SEQ ID NO 107
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 107
aagacgaggg gtcaac                                                      16

<210> SEQ ID NO 108
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 108
cgtcagttaa gacgtc                                                      16

<210> SEQ ID NO 109
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 109
taattctgga tgacgt                                                      16

<210> SEQ ID NO 110
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 110
tgagtacgat tagcct                                                      16

<210> SEQ ID NO 111
<211> LENGTH: 16
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 111
tcatcgttaa caggct                                                         16

<210> SEQ ID NO 112
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 112
agtcgtatct tgagtc                                                         16

<210> SEQ ID NO 113
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 113
tctgatatga cgactc                                                         16

<210> SEQ ID NO 114
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphate

<400> SEQUENCE: 114
aacggtgtgc acgaag                                                         16

<210> SEQ ID NO 115
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (30)..(42)
<223> OTHER INFORMATION: n is a, c, g, or t

<400> SEQUENCE: 115
```
nnnnnnnnnn nnncatgcaa gcttggcgtn nnnnnnnnnn nn                           42

<210> SEQ ID NO 116
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (30)..(42)
<223> OTHER INFORMATION: n is a, c, g, or t

<400> SEQUENCE: 116
nnnnnnnnnn nnnacgccaa gcttgcatgn nnnnnnnnnn nn                           42

<210> SEQ ID NO 117
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: n is a, c, g, or t

<400> SEQUENCE: 117
nnnnnnnnnn nnncatgca                                                     19

<210> SEQ ID NO 118
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(23)
<223> OTHER INFORMATION: n is a, c, g, or t

<400> SEQUENCE: 118
agcttggcgt nnnnnnnnnn nnn                                                23

<210> SEQ ID NO 119
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(23)
<223> OTHER INFORMATION: n is a, c, g, or t

<400> SEQUENCE: 119
agcttgcatg nnnnnnnnnn nnn                                                23

<210> SEQ ID NO 120
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature

```
<222> LOCATION: (1)..(13)
<223> OTHER INFORMATION: n is a, c, g, or t

<400> SEQUENCE: 120
nnnnnnnnnn nnnacgcca                                          19

<210> SEQ ID NO 121
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 121
catgcaagct tggcgt                                             16

<210> SEQ ID NO 122
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 122
agagtgcacc ataagcttgg cgtaat                                  26
```